(12) United States Patent
Rotem et al.

(10) Patent No.: US 11,807,895 B2
(45) Date of Patent: Nov. 7, 2023

(54) HIGH-THROUGHPUT DRUG AND GENETIC ASSAYS FOR CELLULAR TRANSFORMATION

(71) Applicants: THE BROAD INSTITUTE, INC., Cambridge, MA (US); DANA-FARBER CANCER INSTITUTE, INC., Boston, MA (US); President and Fellows of Harvard College, Cambridge, MA (US); MASSACHUSETTS INSTITUTE OF TECHNOLOGY, Cambridge, MA (US)

(72) Inventors: Asaf Rotem, Cambridge, MA (US); Kevin Struhl, Cambridge, MA (US); Paul Blainey, Cambridge, MA (US); Liyi Xu, Cambridge, MA (US)

(73) Assignees: THE BROAD INSTITUTE, INC., Cambridge, MA (US); DANA FARBER CANCER INSTITUTE, INC., Boston, MA (US); PRESIDENT AND FELLOWS OF HARVARD COLLEGE, Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 15/560,977

(22) PCT Filed: Mar. 24, 2016

(86) PCT No.: PCT/US2016/024059
§ 371 (c)(1),
(2) Date: Sep. 22, 2017

(87) PCT Pub. No.: WO2016/154459
PCT Pub. Date: Sep. 29, 2016

(65) Prior Publication Data
US 2018/0051319 A1 Feb. 22, 2018

Related U.S. Application Data

(60) Provisional application No. 62/137,693, filed on Mar. 24, 2015.

(51) Int. Cl.
| | |
|---|---|
| *C12Q 1/68* | (2018.01) |
| *G01N 33/50* | (2006.01) |
| *G01N 33/574* | (2006.01) |
| *C12M 1/26* | (2006.01) |

(52) U.S. Cl.
CPC ............ *C12Q 1/68* (2013.01); *G01N 33/5008* (2013.01); *G01N 33/5011* (2013.01); *G01N 33/574* (2013.01); *C12M 33/00* (2013.01)

(58) Field of Classification Search
None
See application file for complete search history.

(56) References Cited

U.S. PATENT DOCUMENTS

| | | | |
|---|---|---|---|
| 2004/0121324 A1* | 6/2004 | Brenner | C12N 15/1065 435/6.14 |
| 2013/0084622 A1* | 4/2013 | Ram | C12M 23/24 435/252.8 |
| 2013/0316392 A1 | 11/2013 | Anant et al. | |
| 2014/0034556 A1* | 2/2014 | Ma | C12M 47/04 209/684 |
| 2014/0079717 A1 | 3/2014 | Cerione et al. | |
| 2014/0302042 A1 | 10/2014 | Chin et al. | |
| 2016/0362684 A1* | 12/2016 | Brandman | C12N 15/1086 |

FOREIGN PATENT DOCUMENTS

| | | |
|---|---|---|
| EP | 1541694 A1 | 6/2005 |
| WO | 2009023742 A2 | 2/2009 |
| WO | 2009023742 A9 | 2/2009 |

(Continued)

OTHER PUBLICATIONS

Fukazawa et al. A Microplate Assay for Quantitation of Anchorage-Independent Growth of Transformed Cells. 1995. Analytical Biochemistry. vol. 228, pp. 83-90. (Year: 1995).*
Kyle et al. "Genistein-Induced Apoptosis of Prostate Cancer Cells is Preceded by a Specific Decrease in Focal Adhesion Kinase Activity" 51 Molecular Pharmacology 193-200 (Year: 1997).*
International Search Report and Written Opinion for International Patent Application No. PCT/US2016/024059, dated Jun. 17, 2016, 13 pages.
Lamar, et al., "The Hippo Pathway Target, YAP, Promotes Metastasis Through its TEAD-Interaction Domain", Proceedings of the National Academy of Sciences, Sep. 11, 2012, pp. 2441-2450.

(Continued)

*Primary Examiner* — Nancy J Leith
(74) *Attorney, Agent, or Firm* — F. Brent Nix, Esq.; Johnson, Marcou, Isaacs & Nix, LLC

(57) ABSTRACT

A method for detecting oncogenic growth and viability, and/or degree of cellular transformation and/or identifying an agent that inhibits cellular transformation is disclosed. The method including: providing a cellular sample, such as a sample of cells obtained from a subject or a cell line; culturing the cellular sample in low attachment conditions; and detecting growth and7or cell viability of the sample, wherein increased growth relative and/or viability relative to a control or control level indicative of basal growth and/or viability indicates cellular transformation. In some embodiments, the method includes introducing a n expression vector into cells of the cellular sample, wherein the expression vector comprises a gene product expression sequence being tested for transformation ability. In some embodiments the cellular sample is contacted with a test agent and growth and/or cell viability of the sample is determined to determine if the agent inhibits transformation.

12 Claims, 26 Drawing Sheets

(56) References Cited

FOREIGN PATENT DOCUMENTS

WO      2009023742 A3    12/2009

OTHER PUBLICATIONS

Voorhoeve, et al., "A Genetic Screen Implicates miRNA-372 and miRNA-373 as Oncogenes in Testicular Germ Cell Tumors", Cell, Mar. 24, 2006, pp. 1169-1181.

Howes, et al., "3-Dimensional Culture Systems for Anti-Cancer Compound Profiling and High-Throughput Screening Reveal Increases in EGFR Inhibitor-Mediated Cytotoxicity Compared to Monolayer Culture Systems", PLOS One, vol. 9, No. 9, Sep. 23, 2014, 11 pages.

Izar, et al., "GILA, a Replacement for the Soft-Agar Assay that Permits High-Throughput Drug and Genetic Screens for Cellular Transformation", Curr. Protoc. Mol. Bill. 116:28.8.1-28.8.12. DOI: 10.1002/cpmb.26, 12 pages.

Rotem, et al., "Alternative to the Soft-Agar Assay that Permits High-Throughput Drug and Genetic Screens for Cellular Transformation", Proceedings of the National Academy of Sciences, vol. 112, No. 18, Apr. 20, 2015, 6 pages.

Tuynman, "Supplementary European Search Report for EP16769710.1 filed Mar. 24, 2016", dated Aug. 13, 2018, 12 pages.

"International Preliminary Report on Patentability for PCT Application No. PCT/US2016/024059", dated Sep. 26, 2017, 1-10.

Imamura, et al., "Comparison of 2D- and 3D-culture models as drug-testing platforms in breast cancer", Oncol Rep. 2015;33(4):1837-43 doi: 10.3892/or.2015.3767 Epub Jan. 29, 2015), 7 pages.

Kazuhisa, et al., ""Transformation of the Yeast, *Saccharomyces carlsbergensis*, Using an Antibiotic Resistance Marker"", Agricultural and Biological Chemistry, vol. 50, No. 5, May 1, 1986 (May 1, 1986), pp. 1177-1182, XP001313315.

Tuynman, "Examination Report issued in EP16769710.1", dated Jul. 11, 2019, 6 pages.

Summons to attend oral proceedings pursuant to Rule 115(1) EPC issued in EP Application No. 16769710.1 filed Mar. 24, 2016, dated Feb. 5, 2021, 9 pages.

Bilsland, et al., "Yeast-based automated high-throughput screens to identify anti-parasitic lead compounds", Open Biology, vol. 3, No. 2, Feb. 1, 2013 (Feb. 1, 2013), p. 120158, XP055710511, ISSN: 2046-2441, DOI: 10.1098/rsob.120158, 13 pages.

Communication pursuant to Article 94(3) EPC issued in EP16769710.1 filed Mar. 24, 2016, dated Jul. 14, 2020.

Bancos et al., "High-Throughput Screening for Growth Inhibitors Using a Yeast Model of Familial Paraganglioma," PLOS One, vol. 8, No. 2, Feb. 22, 2013 (Feb. 22, 2013), p. e56827, XP055710550, DOI: 10.1371 /journal.pone.0056827.

Miao, et al., "Reduction of fatty acid flux results in enhancement of astaxanthin synthesis in a mutant strain of Phaffia rhodozyma," Journal of Industrial Microbiology & Biotechnology; Official Journal of the Society for Industrial Microbiology, Springer, Berlin, DE, vol. 37, No. 6, Mar. 15, 2010 (Mar. 15, 2010), pp. 595-602, XP019809534, ISSN: 14 76-5535.

Hisao, et al., "Transformation of Intact Yeast Cells Treated with Alkali Cations", Journal of Bacteriology, vol. 153, No. 1, Jan. 1, 1983, 6 pages.

Tuynman, "Examination Report issued in EP16769710.1", dated Jan. 9, 2020, 6 pages.

\* cited by examiner

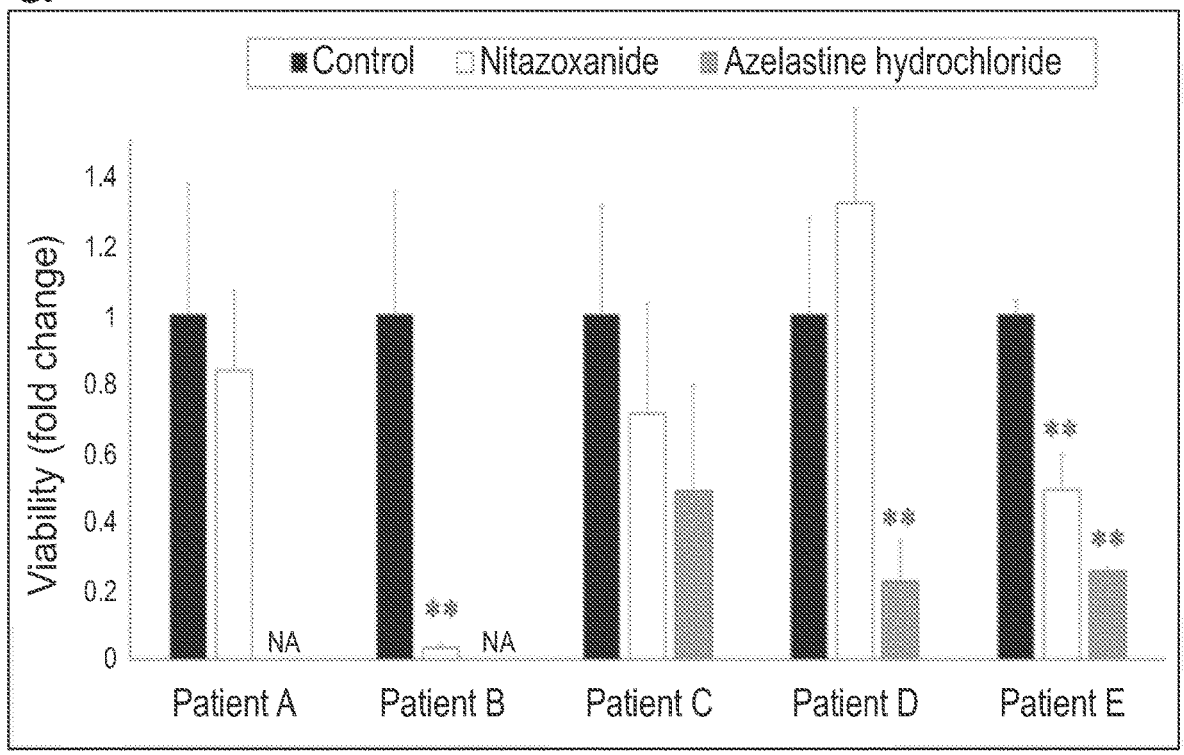
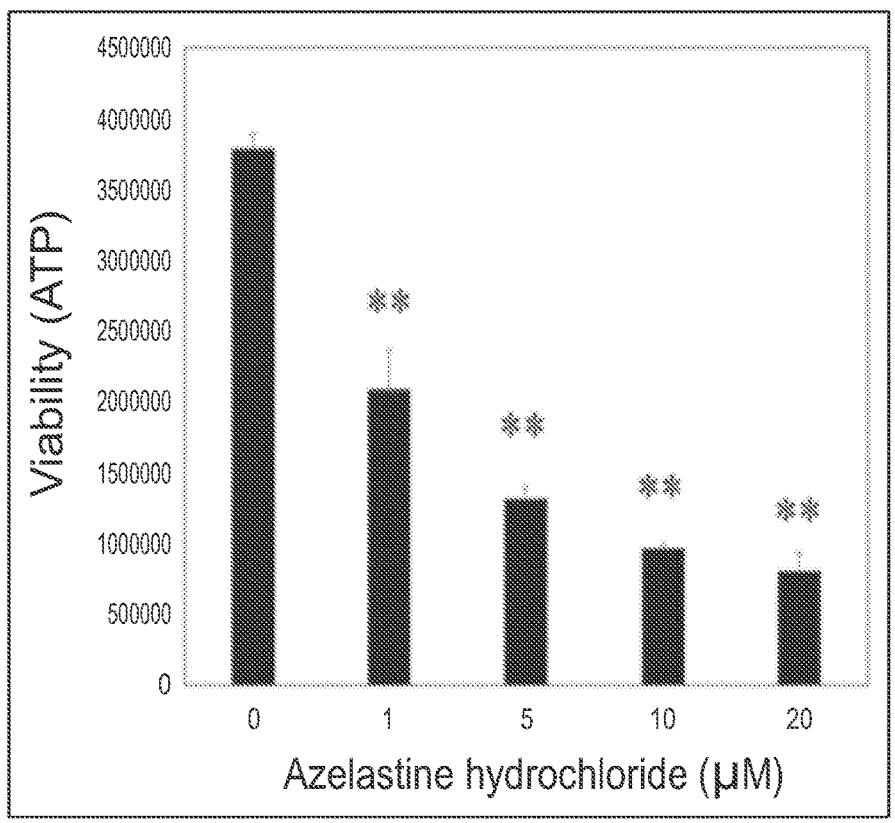
FIG. 4 a

|    | Origin     | Name       | Status          |
|----|------------|------------|-----------------|
| 1  | Fibroblast | EH         | Non-transformed |
| 2  | Fibroblast | EL         | Non-transformed |
| 3  | Fibroblast | ELR        | Transformed     |
| 4  | Fibroblast | WI-38      | Non-transformed |
| 5  | Prostate   | BPH1       | Non-transformed |
| 6  | Prostate   | PC3        | Transformed     |
| 7  | Breast     | MCF-10A    | Non-transformed |
| 8  | Breast     | MDA-MB-231 | Transformed     |
| 9  | Breast     | MDA-MB-468 | Transformed     |
| 10 | Breast     | T47D       | Transformed     |
| 11 | Ovaries    | SAA1       | Transformed     |
| 12 | Ovaries    | SAA2       | Transformed     |
| 13 | Ovaries    | SAA3       | Transformed     |

FIG. 6

Non-transformed lines

| Cell line | GILA | High-attachment | Ratio |
|---|---|---|---|
| EH | 1112 | 99970 | 0.01 |
| BPH1 | 2673 | 205416 | 0.01 |
| MCF10A | 4247 | 100307 | 0.04 |
| EL | 15861 | 185496 | 0.09 |
| Average GILA/High-attachment ratio | | | 0.04 |

Transformed lines

| Cell line | GILA | High-attachment | Ratio |
|---|---|---|---|
| ELR | 67967 | 302034 | 0.23 |
| T47D | 41496 | 46158 | 0.90 |
| PC3 | 28311 | 31278 | 0.91 |
| MDA-MB231 | 9106 | 6642 | 1.37 |
| MDA-MB468 | 26326 | 16076 | 1.64 |
| Average GILA/High-attachment ratio | | | 1.01 |

FIG. 8

| Name | Synonym | Library | Role | p-value (GiLA/HA) |
|---|---|---|---|---|
| SAM001246690 | Honokiol | NIH Clinical Collection 1 - 2013 | Anxiolytic, Antithrombotic, Antidepressant, Antiemetic, Antibacterial, Antitumorigenic, Neuroprotective | 2E-06 |
| SAM001247105 | sibutramine | NIH Clinical Collection 1 - 2013 | Treatment of obesity | 9E-06 |
| SAM001247066 | CGS 12066B | NIH Clinical Collection 1 - 2013 | Antidepressants; Anxiolytics; and in the treatment of migraine disorders | 2E-05 |
| KIN001-119 | ZSTK474 | Kinase Inhibitor Focused Library | Targeting EGFR and PI3K pathways | 1E-04 |
| KIN001-052 | RepSox | Kinase Inhibitor Focused Library | Yes1 kinase inhibitor, transforming growth factor-beta type I receptor (ALK5) inhibitor | 1E-04 |
| SAM001246708 | Nitazoxanide | NIH Clinical Collection 1 - 2013 | Anti-protozoal, antiviral | 2E-04 |
| CVM-04-060 | STK855495 | Kinase Inhibitor Focused Library | A possible LATS1 inhibitor | 7E-04 |
| SAM001246670 | Calcipotriol | NIH Clinical Collection 1 - 2013 | Treatment of psoriasis | 7E-04 |
| SAM001246662 | Nobiletin | NIH Clinical Collection 1 - 2013 | Antioxidant, anti-inflammatory, anti-carcinogenic | 4E-03 |
| SAM001246645 | Azelastine hydrochloride | NIH Clinical Collection 1 - 2013 | Antihistamine, anti-allergy | 6E-02 |

FIG. 9

| Sample ID | Prior treatments |
|---|---|
| Patient A | Carboplatin/Paclitaxel, Paclitaxel+Bevacizumab, Pazopanib |
| Patient B | Carboplatin/Paclitaxel, Paclitaxel+Bevacizumab, Pazopanib |
| Patient C | Carboplatin/Paclitaxel, Paclitaxel, Pazopanib |
| Patient D | Carboplatin/Paclitaxel, Carboplatin/Gemcitabine/Iniparib, Topocetan, Sapacitabine+Seliciclib, Rucaparib |
| Patient E | Carboplatin/Paclitaxel |

FIG. 10

| Dataset | Pathway Name | SIZE | ES | NES | p-value | FDR q-value |
|---|---|---|---|---|---|---|
| GeneOntology | Kinase Activity | 304 | 0.52 | 2.3 | 0.00E+00 | 0.00E+00 |
| GeneOntology | Protein Serine Threonine Kinase Activity | 165 | 0.56 | 2.3 | 0.00E+00 | 0.00E+00 |
| GeneOntology | Phosphotransferase Activity Alcohol Group as Acceptor | 274 | 0.53 | 2.29 | 0.00E+00 | 0.00E+00 |
| GeneOntology | Protein Kinase Activity | 234 | 0.53 | 2.27 | 0.00E+00 | 0.00E+00 |
| GeneOntology | G Protein Coupled Receptor Activity | 176 | 0.55 | 2.26 | 0.00E+00 | 0.00E+00 |
| GeneOntology | ATP Binding | 109 | 0.57 | 2.24 | 0.00E+00 | 0.00E+00 |
| GeneOntology | Adenyl Nucleotide Binding | 115 | 0.57 | 2.24 | 0.00E+00 | 0.00E+00 |
| GeneOntology | Adenyl Ribonucleotide Binding | 112 | 0.57 | 2.23 | 0.00E+00 | 0.00E+00 |
| Reactome | Signaling by ERBB2 | 71 | 0.67 | 2.44 | 0.00E+00 | 0.00E+00 |
| Reactome | Signaling by EGFR in Cancer | 70 | 0.66 | 2.38 | 0.00E+00 | 0.00E+00 |
| GeneOntology | Rhodopsin Like Receptor Activity | 127 | 0.54 | 2.19 | 0.00E+00 | 9.40E-05 |
| GeneOntology | Phosphoinositide Mediated Signaling | 41 | 0.67 | 2.2 | 0.00E+00 | 1.00E-04 |
| GeneOntology | G Protein Signaling Coupled to IP3 Second Messengerphosphilpase C Activating | 40 | 0.68 | 2.22 | 0.00E+00 | 1.20E-04 |
| GeneOntology | Transferase Activity Transerring Phosphorus Containg Groups | 343 | 0.49 | 2.16 | 0.00E+00 | 2.40E-04 |
| GeneOntology | Magnesium Ion Binding | 50 | 0.63 | 2.16 | 0.00E+00 | 2.60E-04 |
| Reactome | Gastrin CREB Signaling Pathway via PKC And MAPK | 166 | 0.56 | 2.28 | 0.00E+00 | 4.00E-04 |
| Reactome | Downstream Signaling Of Activated FGFR | 67 | 0.62 | 2.25 | 0.00E+00 | 5.90E-04 |

From 11A

| | | | | | |
|---|---|---|---|---|---|
| KEGG | Neuroactive Ligand Receptor Interaction | 237 | 0.52 | 2.24 | 0.00E+00 | 5.90E-04 |
| Reactome | Signaling by FGFR in Disease | 85 | 0.59 | 2.22 | 0.00E+00 | 5.90E-04 |
| GeneOntology | Second Messenger Mediated Signaling | 141 | 0.52 | 2.1 | 0.00E+00 | 6.00E-04 |
| KEGG | ERBB Signaling Pathway | 70 | 0.61 | 2.19 | 0.00E+00 | 6.30E-04 |
| Reactome | Downstream Signal Transduction | 63 | 0.63 | 2.25 | 0.00E+00 | 6.70E-04 |
| Reactome | Signaling by ERBB4 | 65 | 0.62 | 2.22 | 0.00E+00 | 7.10E-04 |
| KEGG | Insulin Signaling Pathway | 104 | 0.55 | 2.18 | 0.00E+00 | 7.60E-04 |
| Reactome | Signaling by FGFR | 77 | 0.61 | 2.25 | 0.00E+00 | 7.80E-04 |
| Reactome | Signaling by PDGF | 70 | 0.6 | 2.17 | 0.00E+00 | 7.80E-04 |
| Reactome | Class A1 Rhodopsin Like Receptors | 268 | 0.51 | 2.23 | 0.00E+00 | 7.90E-04 |
| GeneOntology | Protein Amino Acid Phosphorylation | 217 | 0.49 | 2.07 | 0.00E+00 | 9.00E-04 |
| Reactome | GPCR Ligand Binding | 351 | 0.51 | 2.25 | 0.00E+00 | 9.40E-04 |

FIG. 11B

| ORF | GILA | HA | GILA/HA | P-value |
|---|---|---|---|---|
| EGFR | 27.51 | 3.00 | 9.18 | 2E-12 |
| KRAS | 8.70 | 1.65 | 5.28 | 1E-07 |
| HRAS | 6.79 | 1.74 | 3.89 | 1E-05 |
| MRPL20 | 3.36 | 0.87 | 3.88 | 1E-05 |
| EPHB1 | 0.28 | 0.10 | 2.65 | 2E-03 |
| AKT2 | 1.85 | 0.70 | 2.65 | 2E-03 |
| C3orf62 | 1.75 | 0.86 | 2.03 | 2E-02 |
| MAP3K3 | 2.37 | 1.19 | 1.99 | 2E-02 |
| EIF4E | 0.84 | 0.44 | 1.91 | 3E-02 |
| PPP1R8 | 1.78 | 0.96 | 1.86 | 4E-02 |
| HOXC11 | 1.46 | 1.02 | 1.43 | 2E-01 |
| HOXA9 | 2.35 | 1.77 | 1.33 | 3E-01 |
| UBL5 | 0.98 | 0.77 | 1.27 | 4E-01 |
| ARHGEF18 | 1.25 | 1.01 | 1.24 | 4E-01 |
| SOX2 | 2.55 | 2.07 | 1.23 | 5E-01 |
| RARA | 0.72 | 0.58 | 1.22 | 5E-01 |
| S1PR3 | 0.74 | 0.61 | 1.21 | 5E-01 |
| RPL6 | 0.98 | 0.84 | 1.17 | 5E-01 |
| RASA3 | 0.74 | 0.63 | 1.17 | 6E-01 |
| CCL8 | 0.72 | 0.62 | 1.17 | 6E-01 |
| CD40 | 0.85 | 0.73 | 1.17 | 6E-01 |
| RPL39L | 1.25 | 1.08 | 1.17 | 6E-01 |
| BHLHA15 | 1.74 | 1.52 | 1.15 | 6E-01 |
| SOX15 | 0.64 | 0.60 | 1.06 | 8E-01 |
| CSNK1E | 1.05 | 1.00 | 1.05 | 8E-01 |
| BAD | 1.01 | 0.98 | 1.03 | 8E-01 |
| EMR1 | 0.89 | 0.88 | 1.01 | 9E-01 |
| CCDC103 | 0.87 | 0.88 | 0.99 | 9E-01 |
| GSK3A | 0.95 | 1.00 | 0.95 | 1E+00 |
| NUMBL | 0.97 | 1.02 | 0.95 | 1E+00 |
| PRL | 0.76 | 0.83 | 0.92 | 9E-01 |

| | | | | |
|---|---|---|---|---|
| TBP | 0.64 | 0.70 | 0.91 | 9E-01 |
| SOCS3 | 1.05 | 1.19 | 0.88 | 8E-01 |
| ZNF581 | 0.74 | 0.86 | 0.86 | 7E-01 |
| MRPL28 | 0.84 | 1.02 | 0.83 | 6E-01 |
| MRPL33 | 0.83 | 1.02 | 0.82 | 6E-01 |
| CBX6 | 0.99 | 1.21 | 0.81 | 6E-01 |
| PRIM1 | 0.99 | 1.23 | 0.81 | 6E-01 |
| MTM1 | 1.00 | 1.25 | 0.80 | 6E-01 |
| RAB8B | 1.15 | 1.46 | 0.79 | 5E-01 |
| EGFR* | 0.86 | 1.13 | 0.76 | 5E-01 |
| AKAP7 | 0.79 | 1.09 | 0.73 | 4E-01 |
| TCF25 | 0.62 | 0.87 | 0.72 | 3E-01 |
| BCL7A | 0.75 | 1.06 | 0.71 | 3E-01 |
| AGTR1 | 0.63 | 0.90 | 0.70 | 3E-01 |
| SNRK | 0.42 | 0.61 | 0.70 | 3E-01 |
| BAG4 | 0.62 | 0.89 | 0.69 | 3E-01 |
| IFT57 | 0.99 | 1.45 | 0.68 | 3E-01 |
| EGR2 | 0.96 | 1.43 | 0.67 | 3E-01 |
| IRAK1 | 0.90 | 1.37 | 0.66 | 2E-01 |
| HPRT1 | 1.53 | 2.35 | 0.65 | 2E-01 |
| APP | 0.50 | 0.77 | 0.65 | 2E-01 |
| MZF1 | 0.47 | 0.76 | 0.62 | 2E-01 |
| HIST1H4L | 0.82 | 1.33 | 0.62 | 2E-01 |
| HEYL | 0.42 | 0.70 | 0.60 | 1E-01 |
| NTSR1 | 0.68 | 1.13 | 0.60 | 1E-01 |
| SPHK1 | 0.51 | 0.86 | 0.59 | 1E-01 |
| APH1A | 0.44 | 0.80 | 0.55 | 8E-02 |
| CXCL1 | 0.61 | 1.26 | 0.48 | 3E-02 |
| SRC | 0.38 | 1.01 | 0.38 | 3E-03 |
| NUAK2 | 0.54 | 1.64 | 0.33 | 7E-04 |

FIG. 12B

HIGH-THROUGHPUT DRUG AND GENETIC ASSAYS FOR CELLULAR TRANSFORMATION

CROSS-REFERENCE TO RELATED APPLICATIONS

This application is a U.S. National Stage of International Application No. PCT/US2016/024059, filed Mar. 24, 2016, published in English under PCT Article 21(2), which claims the benefit of U.S. Ser. No. 62/137,693, filed on Mar. 24, 2015. The entire contents of the above-identified priority application are hereby fully incorporated herein by reference.

FIELD OF THE DISCLOSURE

The present disclosure relates to methods of and assays for high-throughput drug and cellular transformation screening and specifically for assays based on conditions of cellular non-attachment as a replacement for soft-agar. The subject matter disclosed herein is directed to methods and materials for genome-wide screening of genetic perturbations combined with imaging assays for complex phenotypes to identify relationships between genotypes and phenotypes.

BACKGROUND

For nearly 50 years, the gold-standard assay for cellular transformation/tumorigenicity has been the soft-agar assay (see Macpherson & Montagnier (1964) Agar suspension culture for the selective assay of cells transformed by polyoma virus. Virology 23:291-294; Shin S I, Freedman V H, Risser R, & Pollack R (1975); Tumorigenicity of virus transformed cells in nude mice is correlated specifically with anchorage independent growth in vitro. Proc. Natl. Acad. Sci. U.S.A. 72(11):4435-4439). This classic assay requires that cells grow in an anchorage independent manner, a hallmark of cancer cells, but not normal cells. As such, growth in soft agar is strongly correlated to tumorigenicity in animals. Compared to cells grown in monolayers attached to plates, such three dimensional growth conditions more accurately reflect the natural environment of cancer cells (Pampaloni et al. (2007) The third dimension bridges the gap between cell culture and live tissue. Nat. Reviews Mol. Cell. Biol. 8:839-845) and are crucial to be performed before animal studies (Abbott (2003) Cell culture: biology's new dimension. Nature 424(6951):870-872; Shield K, Ackland M L, Ahmed N, & Rice G E (2009) Multicellular spheroids in ovarian cancer metastases: Biology and pathology. Gynecol. Oncol. 113(1):143-148). However, the soft-agar assay is slow, labor-intensive, imprecise, inconsistent due to subjective definitions of colonies, and not suitable for high-throughput screens.

Unlike non-transformed cells, transformed cells can grow in multi-well plates that are coated with poly(2-hydroxyethyl methacrylate)(poly-HEMA) that prevent cell attachment to the surface (Fukazawa et al. (1995) "A microplate assay for quantitation of anchorage-independent growth of transformed cells." Anal. Biochem. 228(1):83-90). However, it is unclear whether growth on such low-attachment plates is comparable to the soft agar assay, as very few cell lines were tested and quantitative analysis was not described. While it is well recognized that different culture plate surfaces promote distinct growth characteristics of malignant and non-transformed cells, drug and genetic screens are routinely performed on standard plates that permit efficient attachment. Hence, there is a need for better screens to assess drug sensitivity and growth characteristics of transformed and tumorigenic cells under conditions that better mimic a 3-D environment.

A cancer is different for different individuals with respect to the constellation of mutations, methylated tumor suppressor genes, and epigenetic states. As a consequence, the phenotype of every individual cancer may be unique, particularly the response of a patient to drugs. As such, there is an increased interested in developing methods for personalized medicine, in which tumor cells from individual patients are tested for sensitivity to a panel of drugs. Furthermore, many drugs that are in clinical use for other diseases (e.g. metformin for diabetes, various anti-inflammatory drugs, simvastatin for heart disease) have anti-cancer effects in vitro (Hirsch et al. (2010) "A transcriptional signature and common gene networks link cancer with lipid metabolism and diverse human diseases." Cancer Cell 17:348-361) and hence have the potential to be repurposed for treating cancer patients. For these reasons, there is a need for novel assays that are able to provide meaningful results from small numbers of cells in a patient sample, and screen patient-derived tumor cells for their response to a wide variety drugs.

SUMMARY

As disclosed herein the inventors describe an assay in which growth of cells in low attachment (termed GILA) is quantitated, for example by measuring cell viability markers in permeabilized cells. As demonstrated herein GILA is a rapid and quantitative assay for growth, such as oncogenic growth and viability of transformed, or potentially transformed cells, that correlates strongly with the soft agar assay. Using embodiments of the disclosed assay, high-throughput drug screens for drugs that inhibit oncogenic growth or viability of transformed cells may be performed, as well as genetic screens for genes that increase cellular transformation or tumorigenicity. Further, the inventors used their assay to identify drugs that selectively inhibit the growth of fresh, patient-derived cancer cells that are refractory to conventional chemotherapeutic treatment, emphasizing the potential of this approach for personalized medicine.

Disclosed herein is a method for detecting the presence of at least one transformed cell in a sample. In one example embodiments, the method comprises providing a sample comprising at least one cell, such as a sample of cells obtained from a subject or a cell line, culturing the cellular sample in low attachment conditions, and detecting growth and/or cell viability of the sample, wherein increased growth and/or viability relative to a control, or relative to a control level that is indicative of basal growth and/or viability, indicates the presence of at least one transformed cell in the sample. In some embodiments, the method includes introducing an expression vector into cells of the sample, wherein the expression vector encodes at least one genetic perturbation or at least one gene product being tested for transformation ability, such as a known oncogene or gene of unknown oncogenic potential.

In certain embodiments, cells from the sample are aliquoted into one or more containers, such as the wells of a standard or a low attachment microtiter plate or the mixing circuits of a microfluidic device. In certain examples, a container is a well of a microtiter plate and the cells in the microtiter plate are agitated or otherwise mixed to inhibit attachment to the surface of the microtiter plate. In certain examples, a container is a mixing circuit of a microfluidic device. In certain embodiments, the mixing circuit includes one or more valves configured to act in concert to circulate the cells around the mixing circuit, thereby inhibiting attachment of the cells to internal surfaces of the microfluidic device.

Also disclosed is a method of identifying an agent that inhibits growth, such as oncogenic growth and/or viability of transformed or tumorigenic cells. In one example embodiment the method comprises providing a sample of transformed cells and/or cells obtained from the tumor of a subject, culturing the cells from the sample in low attachment conditions, contacting the cultured cells with at least one test agent, and detecting growth modulation and/or cell viability of the cells in the sample, wherein decreased growth and/or viability relative to a control not contacted with the agent, or relative to a control level that is indicative of basal growth and/or viability identifies the agent as one that inhibits oncogenic growth or decreases viability of transformed or tumorigenic cells.

BRIEF DESCRIPTION OF THE DRAWINGS

FIG. 3A, Kinase inhibitors and FDA-approved drugs were screened for their ability to affect transformed cells growing either on high- or low-attachment surface. Drugs specifically affecting the transformed state would inhibit anchorage-independent growth as assayed by GILA, but have little effect on high-attachment conditions among the 633 drugs, 10 drugs were found to be selectively effective against cells that were growing on a low-attachment surface. FIG. 3B, shows the results of a secondary screen to the 10 hits confirming the specific inhibitory role of the compounds in anchorage-independent growth (GILA). FIG. 3C, show the result of validation assays demonstrating that the candidate drugs inhibited fibroblast colony formation in soft agar assays.

FIGS. 4A and 4B are a set of bar graphs showing ex vivo drug sensitivity. (FIG. 4A) Representative results of drug activity of compounds established in initial drug screen in ex-vivo GILA of ovary cancer patient derived cells. Azelastine hydrochloride was found to be highly effective at inhibiting growth of these cells. (FIG. 4B) Azelastine hydrochloride concentration-dependent viability of ovary cancer patient derived cells.

(FIG. 5A) Overrepresentation of 181 barcoded ORFs under low attachment (dark gray shaded region on left) or 201 ORFs under high-attachment (black shaded region on right) conditions. (FIG. 5B) Validation of chosen ORFs by growth on low- and high-attachment surfaces. The ORFs show an increased (>1) growth in low-attachment over time and a preferred growth in low-attachment over growth on high-attachment surfaces (value of GILA/High-attachment ratio larger than 1). Values are fold changes of growth at day 0 to day 5.

FIG. 6 is a table showing cells that were tested in SA and GILA (see FIG. 1), with their origin tissue and transformation status.

FIG. 8 is a table showing non- and transformed cell lines in the values of growth (ATP units) and GILA to high-attachment ratio.

FIG. 9 is a table showing the top 10 compounds with a significant inhibitory effect on growth of transform cells in lower attachment condition. At the right column are p-values of viability measured by comparing GILA to growth in high-attachment.

FIG. 10 is a table showing samples of GILA FDA-approved drug sensitivity assay, details of patients. Previous treatments to ovarian cancer patients are shown. Freshly discarded ascites from these five individuals were used to test drug sensitivity.

FIG. 11 is a table showing gene set enrichment based on rank-ordered low:high attachment growth ratios.

FIG. 12 is a table showing the values of GILA and high attachment growth over five days (fold change) of MCF-10 cell lines stably expressing chosen ORFs along with p-values indicating statistical significance for preferential growth under GILA conditions.

DETAILED DESCRIPTION

I. Terms

Figure 1:
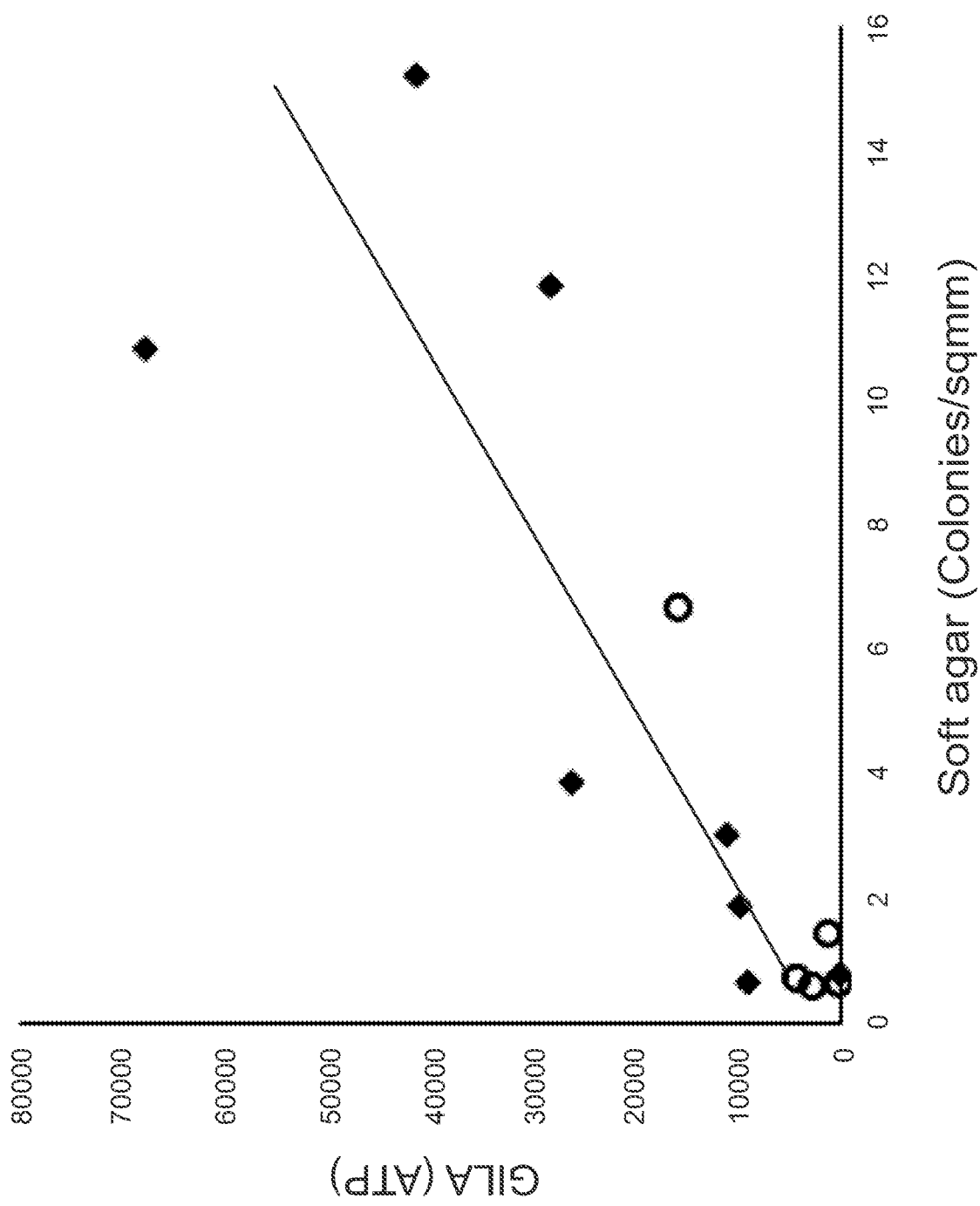
FIG. 1 is a graph showing the correlation between colony formation of cells grown in soft agar (SA) and ATP values as indicative of growth in a GILA low attachment assay. Scatter diagram of transformation values for cells, as resulted from both SA and GILA assays, shows a strong correlation, indicating the comparability of these assays. Each point represents 3 independent repeats of each assay for cell line.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

As used herein, the singular forms "a," "an," and "the," refer to both the singular as well as plural, unless the context clearly indicates otherwise. As used herein, the term "comprises" means "includes." Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the disclosure, the following explanations of terms are provided:

Animal: Living multi-cellular vertebrate organisms, a category that includes, for example, mammals. The term mammal includes both human and non-human mammals. Similarly, the term "subject" includes both human and veterinary subjects.

Cancer: A malignant disease characterized by the abnormal growth and differentiation of cells. "Metastatic disease" refers to cancer cells that have left the original tumor site and migrate to other parts of the body for example via the bloodstream or lymph system.

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia, and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (such as adenocarcinoma), lung cancers, gynecological cancers (such as, cancers of the uterus (e.g., endometrial carcinoma), cervix (e.g., cervical carcinoma, pre-tumor cervical dysplasia), ovaries (e.g., ovarian carcinoma, serous cystadenocarcinoma, mucinous cystadenocarcinoma, endometrioid tumors, glioblastoma, clear cell carcinoma, unclassified carcinoma, granulosa-thecal cell tumors, Sertoli-Leydig cell tumors, dysgerminoma, malignant teratoma), vulva (e.g., squamous cell carcinoma, intraepithelial carcinoma, adenocarcinoma, fibrosarcoma, melanoma), vagina (e.g., clear cell carcinoma, squamous cell carcinoma, botryoid sarcoma), embryonal rhabdomyosarcoma, and fallopian tubes (e.g., carcinoma)), prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma), and skin cancer (such as melanoma and non-melonoma).

Chemotherapeutic agents: Any chemical agent, or non-chemical agent, such as an immunotherapeutic agents/non-chemical agent, with therapeutic usefulness in the treatment of diseases characterized by abnormal cell growth. Such diseases include tumors, neoplasms, and cancer as well as diseases characterized by hyperplastic growth such as psoriasis. Chemotherapeutic agents are described for example in Slapak and Kufe, *Principles of Cancer Therapy*, Chapter 86 in Harrison's Principles of Internal Medicine, 14th edition; Perry et al., Chemotherapy, Ch. 17 in Abeloff, *Clinical Oncology* 2nd ed., 2000 Churchill Livingstone, Inc; Baltzer and Berkery. (eds): *Oncology Pocket Guide to Chemotherapy,* 2nd ed. St. Louis, Mosby-Year Book, 1995; Fischer Knobf, and Durivage (eds): *The Cancer Chemotherapy Handbook,* 4th ed. St. Louis, Mosby-Year Book, 1993. Combination chemotherapy is the administration of more than one agent to treat cancer. In certain examples, a test agent is identified with the methods disclosed herein as a chemotherapeutic agent or potential chemotherapeutic agent.

Contacting: Placement in direct physical association, including both in solid or liquid form, for example contacting a sample, such as a cellular sample, with a test agent according to the method described herein.

Conditions sufficient to detect: Any environment that permits the detection of the desired activity, for example, that permits detection of a phenotype of a cell, such as transformation.

Control: A reference standard. In some examples, a control can be a known value indicative of basal growth and/or viability under certain culture conditions. In other examples, a control in growth and/or viability of a sample, such as a sample of cells, not treated with a test agent. A difference between a test sample and a control can be an increase or conversely a decrease. The difference can be a qualitative difference or a quantitative difference, for example a statistically significant difference. In some examples, a difference is an increase or decrease, relative to a control, of at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Sample: A sample, such as a biological sample, is a sample that includes biological materials (such as cells). In some examples, a biological sample is obtained from an organism or a part thereof, such as an animal. In particular embodiments, the biological sample is obtained from an animal subject, such as a human subject. A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a cellular sample, for example a cellular obtained from the tumor of a subject. In some examples a sample is cells of a cell line.

Test agent: Any agent that is tested for its effects, for example its effects on transformation of a cell. In some embodiments, a test agent is a chemical compound, such as a chemotherapeutic agent or even an agent with unknown biological properties.

Transformation or Malignant Transformation: The process by which cells acquire the properties of cancer. This may occur as a primary process in normal tissue, or secondarily as malignant degeneration of a previously existing benign tumor.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology,* Greene Publishing Associates, 1992 (and Supplements to 2000); Ausubel et al., *Short Protocols in Molecular Biology: A Compendium of Methods from Current Protocols in Molecular Biology,* 4th ed., Wiley & Sons, 1999; Harlow and Lane, *Antibodies: A Laboratory Manual,* Cold Spring Harbor Laboratory Press, 1990; and Harlow and Lane, *Using Antibodies: A Laboratory Manual,* Cold Spring Harbor Laboratory Press, 1999. In addition, the materials, methods, and examples are illustrative only and not intended to be limiting.

II. Description of Several Embodiments

A Introduction

The ability of cells to grow in soft agar is the gold standard and defining assay for oncogenic growth and viability that has been in routine use for decades. As disclosed herein the growth in low attachment (GILA) assay, which likewise requires cells to grow in an anchorage independent manner under conditions of low attachment, exhibits results similar to the soft agar assay. Thus as disclosed herein, the inventors have developed an assay that has the potential to replace the more cumbersome 50-year old soft agar assay. By analyzing a variety of developmentally different cell lines, the inventors have shown that the GILA assay is at least comparable, both qualitatively and quantitatively, to the classic soft-agar assay. The disclosed assay shows superior aspects when compared to the classical soft agar assay. For example GILA is much faster (5 days instead of 3 weeks), much less labor-intensive, more practical (takes up less space in tissue culture incubators), more quantitative, and easier to score using conventional plate readers. For at least these reasons, GILA offers a viable replacement for the soft agar assay method of monitoring cellular transformation.

Conceptually, it is useful and common in the cancer field to consider cells to exist in two distinct states, non-transformed or transformed, with these states being determined experimentally by the soft agar assay. In reality, cellular transformation and cancer is not a single cellular state, but rather encompasses a continuum of phenotypes between the extremes of non-transformed and transformed states. The quantitative nature of the GILA assay is useful in this regard, as transformed cells can vary significantly in how well they grow on low attachment conditions. Thus, the GILA assay can measure the degree of transformation for cell lines subjected to experimental perturbations on a population basis, something that is more difficult and more arbitrary to do with the soft agar assay.

In addition to its advantages over the standard soft agar assay for analyzing a limited number of cell lines and experimental perturbations, the GILA assay is suitable for high-throughput drug or genetic screens. Unlike screens relying on growth of cancer cells per se, the conditions of the GILA assay are more specific and relevant to the transformed state, because they depend on a property of cancer cells that is not shared by normal or non-transformed cells. Furthermore, the combination of a GILA-based screen with a secondary screen that measures growth under conditions of attachment offers additional advantages. For example, drugs that inhibit growth in the GILA assay but not under standard conditions would be missed by a conventional screen, yet they are of potential interest as anti-cancer agents. Conversely, drugs that inhibit growth under both conditions may just be generally toxic to cells. For genetic screens, it is of particular interest to identify genes or genetic perturbations that specifically inhibit or stimulate transformation in a manner that is distinct from cellular proliferation per se.

Furthermore, as cancer cells can be genetically, epigenetically, and phenotypically distinct, it is now well recognized that cancer treatment needs to become personalized to each subject. Furthermore, many drugs in clinical use for other diseases (e.g. diabetes, various inflammatory conditions, heart disease) have anti-cancer effects in vitro (Hirsch H A, et al. "A transcriptional signature and common gene networks link cancer with lipid metabolism and diverse human diseases." Cancer Cell, 2010 17:348-361) and hence have the potential to be repurposed for treating cancer patients. For example, epidemiological data and preclinical experiments suggest the use of diabetes drug metformin for cancer prevention and treatment in non-diabetics (Hirsch H A, Iliopoulos D, Tsichlis P N, & Struhl K. "Metformin selectively targets cancer stem cells and acts together with chemotherapy to blocks tumor growth and prolong remission." Cancer Res. 2009, 69:7507-7511; Pollak M. "Potential applications for biguanides in oncology." J Clin Invest, 2013 123:3693-3700; Morales D R & Morris A D, "Metformin in cancer treatment and prevention" Annu. Rev. Med. 2014, 66:in press), and clinical trials are in progress. For these reasons, the GILA assay offers a phenotypic approach to personalized medicine in which patient-derived tumor cells can be screened for their response to test agents, including a wide variety of FDA-approved drugs. In principle, FDA-approved drugs that inhibit specific cancer cells from a subject could be used off-label, individually or in combination, to treat that subject. This phenotypic approach is complementary to a genetic approach that utilizes DNA sequencing of a patient sample to identify putative oncogenes that confer sensitivity to drugs designed to specifically inhibit the identified oncoprotein.

B. Assays and Methods

Disclosed is a method for detecting cellular transformation, which can be used to supplant the traditional soft agar assay. The methods include providing a cellular sample, for example a sample obtained from a subject, such as a tumor sample, and/or a primary or cultured cell line. The cells are then cultured under low attachment conditions. The growth of the cells in the sample, for example cellular proliferation, and/or viability is detected. An increase in growth, such as cellular proliferation, and/or viability, or decrease in apoptosis indicates the presence of at least one transformed cell in a sample. Conversely, a decreased growth and/or viability, or increase in apoptosis indicates that there are no transformed cells in the sample. The growth and/or viability can be compared to a control, such as a control sample of cells known to be transformed and/or a sample of cells known not to be transformed, for example the relative growth and/or viability of the cells as compared to control or control level indicative of basal growth and/or viability indicates cellular transformation. In some examples, a control is sample, such as a cellular sample that has been grown in high attachment conditions. For example, a sample that is grown in high attachment conditions can be used to test the toxicity of a test agent, such as a compound that inhibits growth and/or viability of cells that have undergone transformation. A test agent that inhibits the growth and/or viability of transformed cells but is toxic may not be a good therapeutic candidate.

Typically the culture time of the cellular sample is selected such that differences, if any in growth and/or viability can be detected, for example, between about 1 and about 10 days or fractions thereof, such as about 1 day, 1.5 days, 2 days, 2.5 days, 3, days, 3.5 day, 4, days, 4.5 days, 5 days, 5.5 days, 6 days, 6.5 days, 7, days, 7.5 day, 8 days, 8.5 days, 9 days, 9.5 days or 9.5 days.

In some examples, the method disclosed herein can be used to test the transformation potential of different genetic perturbations, or the impacts of certain genetic perturbations on the efficacy of one or more test agents, such as a therapeutic test agent. For example, a pooled library of transcriptional effectors for introducing one or more genetic perturbations is designed and cloned into a suitable vector. The library may comprise a set of plasmids or other suitable delivery vectors with each delivery vector encoding one or more genetic perturbations. The genetic perturbations may include a gene knock-in, a gene knock-out, one or more nucleotide insertions, deletions, substitutions, or mutations, or a combination thereof. The genetic perturbation may be generated using, for example, CRISPER/Cas9, RNAi (siRNA and shRNA), TALEN, TALE, and Zn finger site specific nucleases, sited directed mutagenesis, other genetic engineering methods known in the art, or a combination thereof. The vectors may further include promoters and selection markers, such as antibiotic resistance markers known in the art.

In certain other example embodiments, a vector may used to introduce one or more gene products, such as a protein and/or nucleic acid gene product, for example when introduced into a host cell, such as a cell line or other cell that does not exhibit anchorage independent growth and/or transformation. Thus in some embodiments of the method, an expression vector is introduced into cells of the cellular sample. The expression vector includes a nucleic acid sequence encoding a gene product, such a protein or RNA sequence, the expression of which is being tested for transformation ability. In some examples, the gene product's expression sequence includes a known oncogene. In some examples, the gene product's transformation potential is unknown. Methods of expressing proteins and/or nucleic acids, in cells, such as mammalian cells are known by those of skill in the art. Expression vectors, including promoters, selection marker and other expression vector elements, can be chosen for the specific application, such as compatibility with cells and/or cells lines.

In some examples, the expression vectors described above for introducing genetic perturbations or gene products in the proceeding paragraphs may further include a nucleic acid barcode, for example to aid in purification of the vector and/or identification of the expression sequence. Nucleic acid barcodes are used to tag DNA, RNA, or other molecules in an identifiable way. Barcodes can be any nucleic acid sequence that may be used to identify a particular tagged molecule. Barcoding methods have been used extensively to allow parallel, multiplexing experimentation of different types of genetic alterations (see, for example, Craig et al., Nat. Methods 5: 887-893, 2008; Gerrits et al., Blood 115: 2610-2618, 2010; and Berns et al., Nature 428: 431-437, 2004). Barcodes that can be used according to the methods of the disclosure can have a length of at least, for example, 4, 5, 6, 7, 8, 9, 10, 11, 12, 13, 14, 15, 16, 17, 18, 19, 20, 21, 22, 23, 24, 30 25, 26, 27, 28, 29, 30, 35, 40, 45, 50, 60, 70, 80, 90, or 100 bp. In some examples, two flanking barcode sequences can be used to design primers for PCR retrieval and/or amplification. Methods for DNA amplification are well-understood in the art. For example, DNA sequences can be amplified by polymerase chain reaction (PCR). PCR primers can be designed based on, for example, barcode or scar sequences. PCR may be preceded by a restriction digest step that excises the target DNA from a vector. Alternatively, DNA can be amplified by, for example, introduction into cells (for example, bacteria or yeast) with, for example, a self-replicating vector (for example, a plasmid, bacterial artificial chromosome, yeast artificial chromosome, fosmid, or virus) containing the target DNA, followed by clonal expansion of the cells in a suitable growth medium. The amplified vectors can be readily purified from the cells using standard preparation techniques in the art.

In one example embodiment, each vector encodes a unique barcode corresponding to the one or more genetic perturbations or gene products encoded by the vector. Each vector may be introduced into a separate container comprising a cell or population of cells. The barcode may be later isolated and/or amplified to identify the genetic perturbation delivered to a given container or population of cells.

In certain example embodiments, detecting cell growth comprises detecting an increase in cell count within a given container. In certain other example embodiments, cell growth is detected by detecting an increase in one or more biomarkers. The biomarker may be a nucleic acid, or a protein or peptide. In certain example embodiments, cell growth may be measured using a DNA synthesis cell proliferation assay wherein a detectable marker, such as 3H-thymidine or 5-brom-2'-deoxyuridine, is incorporated into newly synthesized DNA, and the levels of the detectable level are assessed. In another example embodiment, cell growth is assessed using a metabolic cell proliferation assay where tetrazolium salts or Alamar Blue are added to the culture medium and reduced by metabolically active cells resulting in a measurable change in the color of the media. Example tetrazolium salts include MTT, XTT, and WST1. In certain other example embodiments, cell growth is detected by detection of certain proliferation markers. Example proliferation markers include Ki-67, proliferating cell nuclear antigen (PCNA), topoisomerase IIB and phosphohistone H3. In another example embodiment, cell growth may be measure by measuring cellular ATP levels where there is a recognized tight linear relationship between cell number and the concentration of ATP. ATP concentrations may be detected, for example, using luciferase and its substrate luciferin. In the presence of ATP, luciferase produces light proportional to ATP concentration. In other example embodiments, cell growth may be measured by detecting levels of apoptosis in cell population, using for example phosphatidylserine exposure assays, caspase, calpain and cathepsin activation assays, assays measuring changes in mitochondrial transmembrane potential, detection of DNA fragmentation levels, and/or detection of cell membrane blebbing and chromatin condensation.

As discussed above, aspects of the disclosed method concern culturing cells in low attachments environments, such as in a container, or vessel that inhibits attachment of the cells to the surface of the container or vessel. In certain examples, a container is a well of a cell culture plate, such as a microtiter plate. One of the discoveries made by the inventors was the low attachment conditions were possible by culturing the cells in an environment where the cells were in a constant state of movement or agitation such that the cells were not able to attach to the surface of a container, such as the wells of a microtiter plate. Thus, in certain embodiments, the method further includes agitating the cells to inhibit attachment to the cell culture plate, for example agitating the cells of the sample, in standard growth conditions of 5% $CO_2$, 37° C., while the cells were rotated, for example in an orbital shaker at between about 400 rpms and about 1200 rpms, such as about 400, about 500, about 600, about 700, about 800, about 900, about 1000, about 1100, or about 1200 rpm (round per minute). In some examples the cells are cultured at a concentration range of about 100 to about 300, cells/well in 96-well plate, such as 100, 110, 120, 130, 140, 150, 160, 170, 180, 190, 200, 210, 220, 230, 240, 250, 260, 270, 280, 290, or 300 cells per well. In some embodiments uncoated microtiter plates, such as polystyrene microtiter plates are used. In some examples, low attachment containers are used, such as coated plates, for example Examples—384-well microplate with Ultra Low-attachment (Sumitomo, PrimeSurface384U), 96-well microplate with low attachment surface (#3474, Corning) and/or plates treated with at least one compound that inhibits cell attachment, for example Poly-Hema and/or phenyl dextran coated plates. In some examples, individual wells of the microtiter plate are treated with different test agents, and/or concentrations of test agents. In certain embodiments, cells from a sample are aliquoted or otherwise sorted into one or more containers, for example so that the resulting portions of cells in each of the containers can be exposed to different conditions, such as different environmental conditions, for example different test agents and/or different concentrations of test agents.

Figure 13:
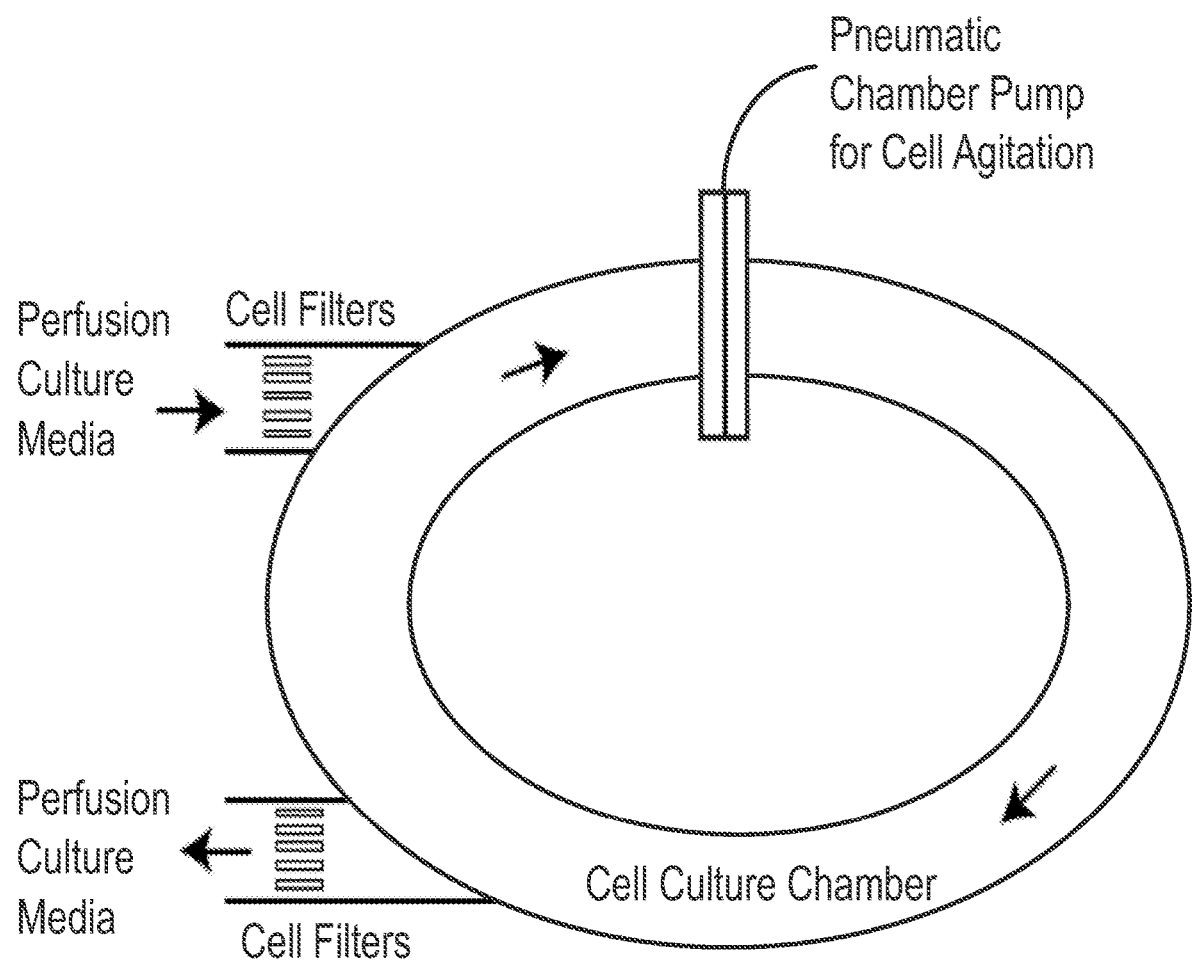
FIG. 13 is a schematic of an exemplary mixing circuit.

Aspects of the disclosed methods include the use of microfluidic devices for analysis of oncogenic growth and viability, and/or degree of cellular transformation within a sample. Thus, in certain embodiments, the containers include one or more mixing circuits of a microfluidic device. An exemplary mixing circuit is given in FIG. 13. In certain embodiments, the method further includes splitting the sample between two or more microfluidic circuits of the microfluidic device. In some embodiments, individual mixing circuits of the microfluidic device are treated and/or contacted with different test agents, and/or concentrations of test agents, for example to expose the cells in the mixing circuit to the test agents. In certain embodiments, the test agent is loaded into the microfluidic circuit mixing circuit, before, after, or concurrent with the sample.

In some embodiments, the mixing circuit includes one or more pumps. For example, peristaltic pumping can be achieved by controlling the open/close sequence of a set of valves. Thus in some embodiments, the mixing circuit includes one or more valves configured to act in concert to circulate the cells around the mixing circuit. The circulating action of the mixing circuit inhibits attachment of the cells to internal surfaces of the microfluidic device. In certain example embodiments, the control channel for each set of valves or filters has pressure inputs on the left and right sides of the microfluidic device. The use of two pressure inputs allow for uniform mixing across the chip by increasing valve actuation time and avoiding delay from the build-up of pressure gradients between mixing circuits across the chip.

In certain embodiments, the microfluidic device further includes a one or more of a holding chamber in fluid communication with the mixing circuit, an output port, and one or more additional valves. In certain embodiments, at least one of the one or more valves is a sieve valve, such as disclosed in International Patent Application No. PCT/US14/58637. In certain embodiments, at least one or more of the valves is a conventional valve. In certain embodiments, at least one valve (such as an input valve) is positioned between the input port and the mixing circuit. In certain embodiments, one or more valves is positioned between the mixing circuit and the holding chamber. In certain embodiments, at least one or more valves is positioned between the mixing circuit and/or the holding chamber and/or the output port. In certain embodiments, at least one or more valves are positioned between two or more mixing circuits. The valves may be elastomeric valves that fully or partially occlude a flow channel when pressure is applied to the elastomeric material. For example, fluid channels may be located above or below a "control" layer of the microfluidic device. The control layer includes an elastomeric membrane that can be deflected to partially or completely block the flow channel. Suitable elastomeric materials include any material having a Young's modulus less than a metal. For example, the valves can have a Young's modulus of less than about 10 gPa, less than about 5 gPa, less than about 1 gPa, less than about 0.1 gPa, less than about 0.01 gPa, or less than about 0.0001 gPa. In certain example embodiments, the valves can have a Young's modulus of between about 200 KPa and 1000 KPa. In certain other example embodiments, about 300 and about 900 KPA. In yet another example embodiment, the valve has a Young's modulus of about 360 to about 870 KPa. In certain example embodiments, the elastomer is made from PDMS, polytetrafluoroethylene (PTFE), urethanes, other silicones, or perfluoropolyethers. Valves can be closed using fluid pressure, gas pressure, or any other suitable mechanism applied through a channel in the control layer and running under the elastomeric membrane to deflect the membrane into the fluid channel. For example, the valves can be actuated by injecting gases (e.g. air, nitrogen, argon), liquids (e.g., water, silicone oils, fluorinated oils, and other oils), solutions containing salts and/or polymers (including, but not limited to, polyethylene glycol, glycerol, and carbohydrates), and the like into the control channel. In addition to elastomeric valves actuated by pressure-based actuation system, monolithic valves with an elastomeric component and electrostatic, magnetic, electrolytic, and electrokinetic actuation systems as discussed, for example, in U.S. Pat. No. 6,767,706 and U.S. Patent Application Publication Nos. 2002/0109114 and 2002/0127736 may be used in certain example embodiments. Valves may also be closed by pressing a pin on the top of the flow channel to collapse the channel. For example, a pin actuated by a step motor or piezoelectric actuator.

Each mixing circuit can include one or more mixing circuits, or rings. A mixing circuit may be formed from two or more flow channels connected together at two or more points. In certain example embodiments, two or more flow channels may be connected by bridge flow channels. Each mixing circuit may further include one or more filters, such as one more filter valves, for example as disclosed in International Patent Application No. PCT/US14/58637.

The one or more mixing circuits may be formed in a networked fashion on the microfluidic device with each node in the network representing one or more mixing circuits. The mixing circuits may also be arranged in a parallel fashion on the microfluidic device.

In certain example embodiments, a microfluidic device may include between 1 and 1000 mixing circuits. In certain example embodiments, the microfluidic device may comprise between approximately 1 and 192, between approximately 1 and 144, between 1 and approximately 96, between 1 and approximately 48, between 1 and approximately 24, between one and approximately 12 mixing circuits. In one example embodiment, the microfluidic device has 96 mixing circuits.

Flow channels, such as flow channels making up a mixing circuit may have a length of approximately 1 mm to approximately 10 mm and an average width of 0.05 mm to 0.4 mm. In certain example embodiments, the flow channels may have a substantially rectangular profile. The bridge flow channels may have a length of approximately 0.2 mm to approximately 1 mm and an average width of approximately 0.1 mm to approximately 0.4 mm. Reaction flow channels may maintain the same width throughout or may vary in width along the length of the reaction or bridge flow channel. A mixing circuit may have a volume of approximately 40 nL to approximately 500 nL, although smaller and larger examples are contemplated.

The bridge and flow channels may have a width selected from the group consisting of: between about 1 μm and about 5 μm, between about 5 μm and about 25 μm, between about 25 μm and about 50 μm, between about 50 μm and about 75 μm, between about 75 μm and about 100 μm, between about 100 μm and about 125 μm, between about 125 μm about 175 μm, between about 175 μm about 225 μm, between about 200 μm and about 225 μm and about 225 μm and about 250 μm, between about 250 μm and about 275 μm, and between about 275 μm and about 300 μm.

The flow and bridge channels may have a height of between about 5 μm and about 10 μm, between about 10 μm and about 15 μm, between about 15 μm and about 20 μm, between about 20 μm and about 25 μm, between about 25 μm and about 30 μm, between about 30 μm and about 35 μm, between about 35 μm and about 40 μm, between about 40 μm and about 45 μm, between about 45 μm and about 50 μm, between about 50 μm and about 55 μm, between about 10 μm and about 400 μm, between about 20 μm and about 400 μm, between about 30 μm and about 400 μm, between about 40 μm and about 400 μm, between about 50 μm and about 400 μm, between about 60 μm and about 400 μm, between about 70 μm and about 400 μm, between about 80 μm and about 400 μm, between about 100 μm and about 400 μm, between about 125 μm and about 400 μm, between about 150 μm and about 400 μm, between about 175 μm and about 400 μm, between about 200 μm and about 400 μm, between about 225 μm and about 400 μm, between about 250 μm and about 400 μm, between about 275 μm and about 400 μm, between about 300 μm and about 400 μm, between about 325 μm and about 400 μm, between about 350 μm and about 400 μm, and between about 375 μm and 400 μm.

The bridge and flow channels can have an aspect of height to width of less than about 1:2, less than about 1:5, less than about 1:10, and less than about 1:15.

In certain example embodiments, filters that may be used in the present disclosure may have features similar to the valves described above, but instead of closing the fluid channel completely, the filter may only partially close the fluid channel, for example, to filter components in the fluid based on size, for example holding cells behind the valve as additional reagents, such as test agent or growth media are introduced into the flow channels of the microfluidic device. In certain example embodiments, the filter may comprise a toothed sieved valve. Toothed sieve valves are disclosed in further detail in International Patent Application No. PCT/US14/58637.

Microfluidic devices disclosed herein may be silicone-based chips and may be fabricated using a variety of techniques, including, but not limited to, hot embossing, molding of elastomers, injection molding, LIGA, soft lithography, silicon fabrication and related thin film processing techniques. Suitable materials for fabricating the microfluidic devices include, but are not limited to, cyclic olefin copolymer (COC), polycarbonate, poly(dimethylsiloxane) (PDMS), and poly(methyl methacrylate) (PMMA). In one embodiment, soft lithography in PDMS may be used to prepare the microfluidic devices. For example, a mold may be made using photolithography which defines the location of flow channels, valves, and filters within a substrate. The substrate material is poured into a mold and allowed to set to create a stamp. The stamp is then seal to a solid support, such as but not limited to, glass.

Due to the hydrophobic nature of some polymers, such as PDMS, which absorbs some proteins and may inhibit certain biological processes, the internal surfaces of the microfluidic device can be coated to reduce attachment of cells to the internal surfaces of the microfluidic device, such as the mixing circuit. Suitable coatings include parylene. Thus in some embodiments, the mixing circuits of the microfluidic device are treated with one or more of parylene, to inhibit attachment, for example to form a coating that inhibits attachments of cells to the internal surfaces of the mixing circuit. Alternatively, agents can be added to culture media to reduce attachment, for example BSA and/or surfactants.

The microfluidic devices may further comprise inlet and outlet ports, or openings, which in turn may be connected to valves, tubes, channels, chambers, and syringes and/or pumps for the introduction and extraction of fluids into and from the microfluidic device. In certain embodiments, the microfluidic device includes an input port in fluid connection with the mixing circuit. The microfluidic devices may be connected to fluid flow actuators that allow directional movement of fluids within the microfluidic device. Example actuators include, but are not limited to, syringe pumps, mechanically actuated recirculating pumps, electroosmotic pumps, bulbs, bellows, diaphragms, or bubbles intended to force movement of fluids. In certain example embodiments, the microfluidic devices are connected to controllers with programmable valves that work together to move fluids through the microfluidic device. In certain example embodiments, the microfluidic devices are connected to the controllers. The microfluidic devices may be connected to flow actuators, controllers, and sample loading devices by tubing that terminates in metal pins for insertion into inlet ports on the microfluidic device.

Figure 18:
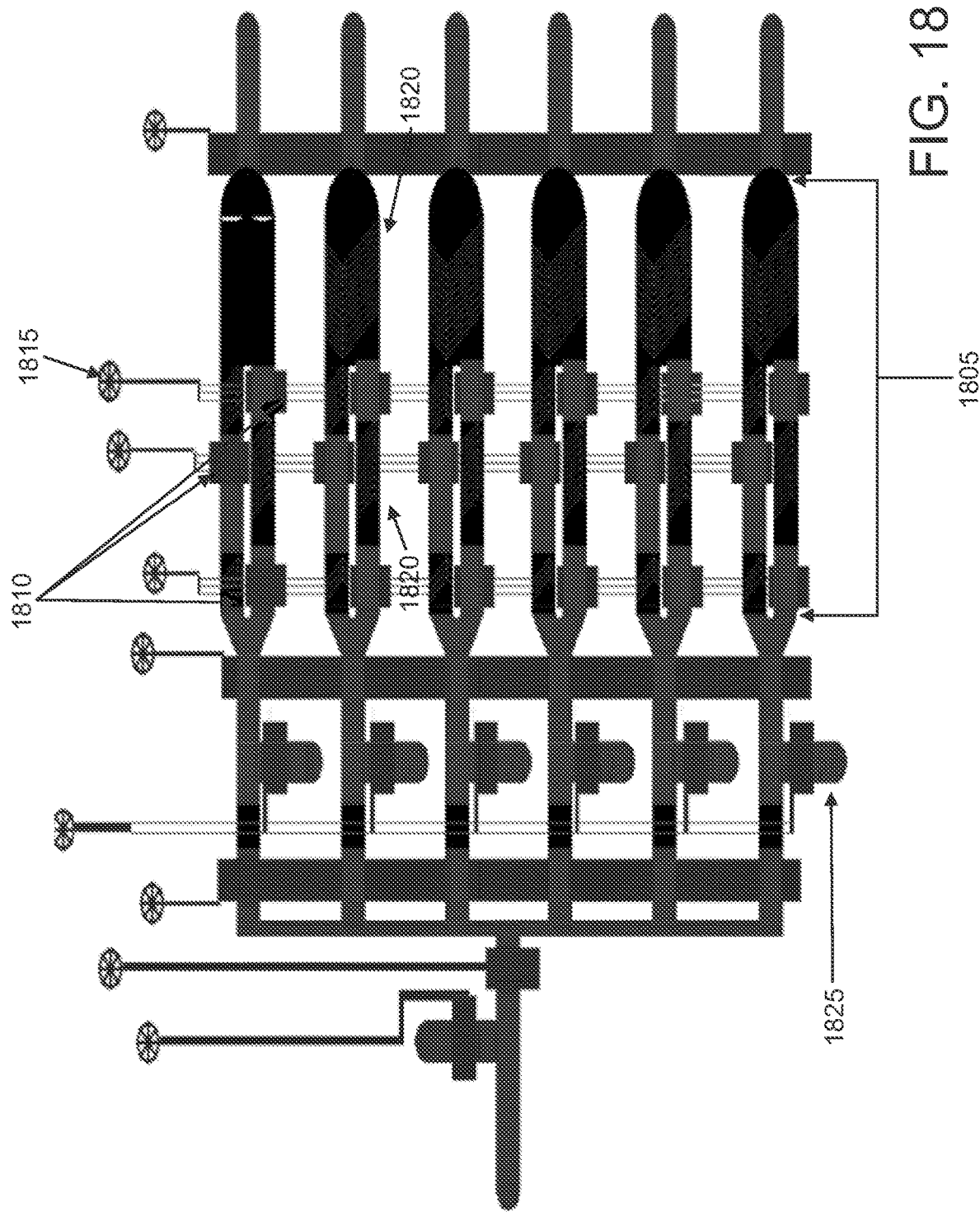
FIG. 18 is a diagram of an example microfluidic device comprising multiple mixing circuits for conducting the assays described herein in accordance with certain example embodiments.

In one exemplary embodiment, a microfluidic device comprising a series of mixing circuits may be used. An example device configuration is shown in FIG. 18. Each reaction circuit 1805 comprises a set of valves 1810 actuated by a corresponding set of pumps 1815. The valves 1810 are opened in sequence to provide peristaltic pumping of cells and culture media through the mixing circuit. In certain example embodiments, the reaction circuit may comprise one or more portions that comprise one or more sets of diagonal engravings 1820. The diagonal engravings enhance perfusion through the mixing circuit. Cells, culture media, and the agent to be screened are introduced into each mixing circuit. Each mixing circuit may be further connected to a tank 1825. The cells are allowed to flow from the mixing circuit into the tank where through the cells are lightly agitated before being returned to the mixing circuit. Agitation may be provided by mixing or by other suitable means. A different agent or combination of agents may be introduced into each mixing circuit. Likewise, a different concentration of an agent or different concentrations of agent combinations may be introduced into each mixing circuit. The 6 mixing circuit device shown in FIG. 18 is exemplary. The device shown in FIG. 18 may be made of the materials described above and comprise channels with dimensions and volumes described above. In certain example embodiments, the device is made out of two layers of PDMS. Accordingly, the number of mixing circuits per device is constrained primarily by the overall size of the device and the number of screens to be carried out in parallel.

Figure 19:
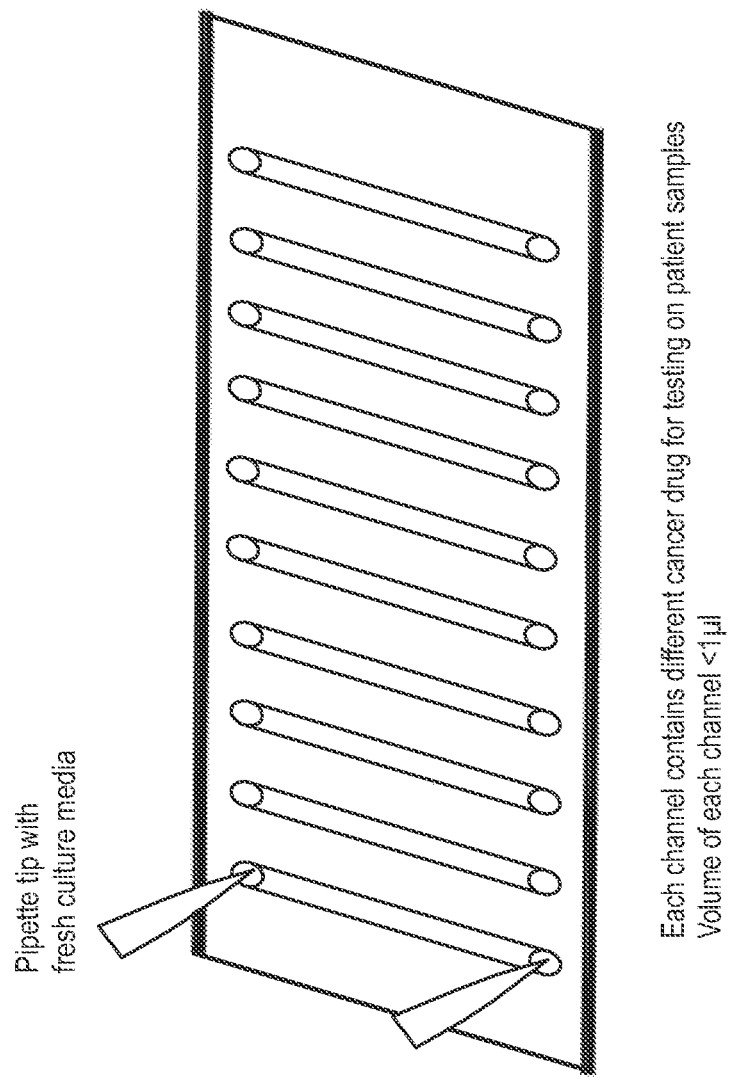
FIG. 19 is a diagram of a device for screening multiple therapeutic agents in parallel, in accordance with certain example embodiments.

In one exemplary embodiment, a multi-channel device may be used to perform the assays described herein. An example device configuration is shown in FIG. 19. The device may be manufactured using the materials described above. In certain example embodiments, the device comprises an upper PDMS layer and a glass bottom layer. The upper PDMS layer may define the channels. The volume of each channel may range from 0.5 µl to 5 µl. In one example embodiment, each channel has a volume of 1 µl. The number of channels per device may vary based on the number of screens to be conducted in parallel. In certain example embodiments, the inner surfaces of each chamber are treated against cell adhesion. Openings are located on either end of the channel. In certain example embodiments, the openings are sized to fit a pipette tip. Cells to be screened are introduced into each chamber along with growth medium and an agent to be tested. A different agent or combination of agents may be introduced into each mixing circuit. Likewise, a different concentration of an agent or different concentrations of agent combinations may be introduced into each mixing circuit. After introduction of the cells, growth medium, and agent(s) to be screened the opening are sealed. In certain example embodiments, the opening are sealed with a container, such as a plastic pipette tip. The container is filled with fresh growth medium. The level of growth medium is filled so that volume of growth medium in each container is not equal thus causing constant perfusion between the two chambers via the channels such that constant cell agitation is achieved.

Figure 20:
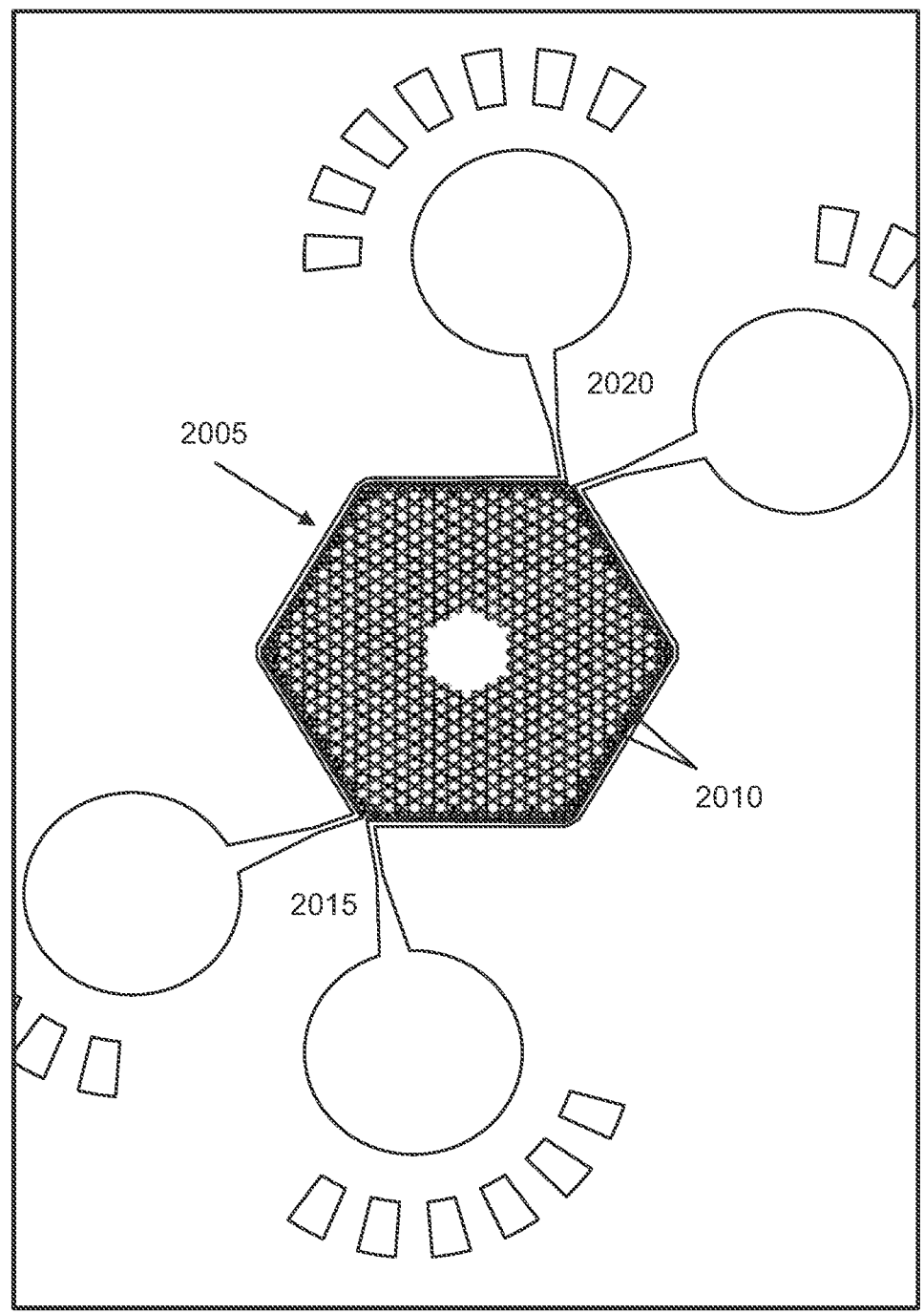
FIG. 20 is a diagram of an example diffusion based microfluidic device for conducting the assays described herein in accordance with certain example embodiments.

In another example embodiment, a diffusion gradient device may be used to perform the assays described herein. An example diffusion gradient device is shown in FIG. 20 and further described in U.S. Provisional Patent Application No. 62/247,344, which is incorporated herein by reference. In brief, the microfluidic device may comprise multiple polygonal chambers 2005. In certain example embodiments, the device is double-sided such that a separate chamber 2005 is defined on both sides of the polygon. In certain example embodiments, the height of each chamber is 100 µm. In certain example embodiments, the width of each chamber is 1.0 mm to 2.0 mm. Each chamber comprises a set of columns 2010 that extend from a bottom surface to a top surface of each culture chamber 2005. The columns 2010 increase perfusion flow through the chamber 2005. The interior surfaces of the chamber 2005 and columns 2010 are treated to prevent cell adhesion. Each chamber 2005 is connected to an inlet, or set of inlets, 2015 and an outlet, or set of outlets, 2020 that can be used to flow cells, culture medium and agents to be tested into the chamber 2005. The chamber results in a diffusion gradient where the agent to be tested is at a higher concentration proximate the inlet and at a lower concentration proximate to the outlet.

Aspects of the disclosed method concern identifying agents that inhibit the growth and/or viability of transformed cells, cellular transformation, cancer growth, and/or tumor growth. Such a method includes providing a cellular sample of transformed cells and/or cells obtained from the tumor of a subject, such as a tumor of a subject suffering from cancer, such as a solid tumor. The cells of the sample are cultured in low attachment conditions. The sample is further contacted with one or more test agents, such as any agent being tested for inhibition of growth and/or viability of transformed cells. Growth and/or cell viability of the sample or determined and/or measured, for example by determining ATP levels, staining, apoptosis and the like. Decreased growth and/or viability relative to a control not contacted with the agent or control level indicative of basal growth and/or viability identifies the agent as one that inhibits growth and/or viability of transformed cells. Conversely increased growth and/or viability relative to a control not contacted with the agent or control level indicative of basal growth and/or viability identifies the agent as one that does not inhibit growth and/or viability of transformed cells. In some embodiments, the control is a standard value. In some embodiments, the control is the amount is the growth and/or viability of a sample not contacted with the agent.

In some embodiments, the cells are transformed with an expression vector comprising a known oncogene, for example to test the effectiveness of agents against the known oncogene. In some embodiments, the expression vector further comprises a nucleic acid barcode to aid in identification of the oncogene. In some embodiments, the agent is tested for antitumor activity. Test agents can be any compound, such as a chemical compound, a small molecule, or an antibody. By exposing cells, or fractions thereof (such as nuclear extract), tissues, or even whole animals, to different members of the chemical libraries, and performing the methods described herein, different members of a chemical library can be screened for their effect on transformation simultaneously in a relatively short amount of time, for example using the high throughput methods disclosed herein.

In some embodiments, screening of test agents involves testing a combinatorial library containing a large number of potential therapeutic compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

Appropriate agents can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

Preparation and screening of combinatorial libraries is well known to those of skill in the art. Libraries (such as combinatorial chemical libraries) useful in the disclosed methods include, but are not limited to, peptide libraries (see, e.g., U.S. Pat. No. 5,010,175; Furka, Int. J. Pept. Prot. Res., 37:487-493, 1991; Houghton et al, Nature, 354:84-88, 1991; PCT Publication No. WO 91/19735), (see, e.g., Lam et al., Nature, 354:82-84, 1991; Houghten et al., Nature, 354:84-86, 1991), and combinatorial chemistry-derived molecular library made of D- and/or L-configuration amino acids, phosphopeptides (including, but not limited to, members of random or partially degenerate, directed phosphopeptide libraries; see, e.g., Songyang et al., Cell, 72:767-778, 1993), antibodies (including, but not limited to, polyclonal, monoclonal, humanized, anti-idiotypic, chimeric or single chain antibodies, and Fab, F(ab')2 and Fab expression library fragments, and epitope-binding fragments thereof), small organic or inorganic molecules (such as, so-called natural products or members of chemical combinatorial libraries), molecular complexes (such as protein complexes), or nucleic acids, encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Natl Acad. Sa. USA, 90:6909-6913, 1993), vinylogous polypeptides (Hagihara et al., J. Am. Chem. Soc, 114:6568, 1992), nonpeptidal peptidomimetics with glucose scaffolding (Hirschmann et al., J. Am. Chem. Soc, 114:9217-9218, 1992), analogous organic syntheses of small compound libraries (Chen et al., J. Am. Chem. Soc, 116:2661, 1994), oligo carbamates (Cho et al., Science, 261:1303, 1003), and/or peptidyl phosphonates (Campbell et al., J. Org. Chem., 59:658, 1994), nucleic acid libraries (see Sambrook et al. Molecular Cloning, A Laboratory Manual, Cold Springs Harbor Press, N Y., 1989; Ausubel et al., Current Protocols m Molecular Biology, Green Publishing Associates and Wiley Interscience, N. Y., 1989), peptide nucleic acid libraries (see, e.g., U.S. Pat. No. 5,539,083), antibody libraries (see, e.g., Vaughn et al., Nat. Biotechnol, 14:309-314, 1996; PCT App. No. PCT/US96/10287), carbohydrate libraries (see, e.g., Liang et al., Science, 274:1520-1522, 1996; U.S. Pat. No. 5,593,853), small organic molecule libraries (see, e.g., benzodiazepines, Baum, C&EN, January 18, page 33, 1993; isoprenoids, U.S. Pat. No. 5,569,588; thiazolidinones and metathiazanones, U.S. Pat. No. 5,549, 974; pyrrolidines, U.S. Pat. Nos. 5,525,735 and 5,519,134; morpholino compounds, U.S. Pat. No. 5,506,337; benzodiazepines, U.S. Pat. No. 5,288,514) and the like.

Libraries useful for the disclosed screening methods can be produced in a variety of manners including, but not limited to, spatially arrayed multipin peptide synthesis (Geysen, et al., Proc. Natl. Acad. Sa., 81(13):3998-4002, 1984), "tea bag" peptide synthesis (Houghten, Proc. Natl. Acad. Sa., 82(15):5131-5135, 1985), phage display (Scott and Smith, Science, 249:386-390, 1990), spot or disc synthesis (Dittrich et al., Bworg. Med. Chem. Lett., 8(17):2351-2356, 1998), or split and mix solid phase synthesis on beads (Furka et al., Int. J. Pept. Protein Res., 37(6):487-493, 1991; Lam et al., Chem. Rev., 97 (2):411-448, 1997).

Devices for the preparation of combinatorial libraries are also commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, for example, ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Libraries can include a varying number of compositions (members), such as up to about 100 members, such as up to about 1,000 members, such as up to about 5,000 members, such as up to about 10,000 members, such as up to about 100,000 members, such as up to about 500,000 members, or even more than 500,000 members. In one example, the methods can involve providing a combinatorial chemical or peptide library containing a large number of potential therapeutic compounds. Such combinatorial libraries are then screened by the methods disclosed herein to identify those library members (particularly chemical species or subclasses) that display a desired characteristic activity.

The compounds identified using the methods disclosed herein can serve as conventional "lead compounds" or can themselves be used as potential or actual therapeutics. In some instances, pools of candidate agents can be identified and further screened to determine which individual or sub-pools of agents in the collective have a desired activity. Compounds identified by the disclosed methods can be used as therapeutics or lead compounds for drug development for a variety of conditions.

Control reactions can be performed in combination with the libraries. Such optional control reactions are appropriate and can increase the reliability of the screening. Accordingly, disclosed methods can include such a control reaction.

EXAMPLES

Example 1

A Replacement for the Soft-Agar Assay that Permits High-Throughput Drug and Genetic Screens for Cellular Transformation This example describes the development of the assays for measuring oncogenic growth and viability, and/or degree of cellular transformation of a sample, including a patient sample or a cell line, without the need for soft agar plates.
Results
The GILA Assay is Comparable to the Soft-Agar Assay.

The principle of GILA is that transformed cells can grow on low-attachment plates, whereas non-transformed cells cannot. A critical parameter for the GILA assay is cell density (number of cells/well), and for these experiments, this was optimized at 1000 cells/well in 100 μl medium for 96-well plates or 50 cells/well in 30 μl growth medium for 384-well plates. 13 cell lines originating from 4 different tissues-fibroblast, breast, ovary and prostate were examined (FIG. 6). An equal number of cells from each line were seeded into wells of an ultra-low attachment 96-well plate, grown for 5 days, and assayed for ATP levels as a surrogate for number of viable cells. As expected, the transformed cells grew significantly better than non-transformed cells (FIG. 7), with 5-30 fold increased ATP levels (FIG. 1).

Figure 7:
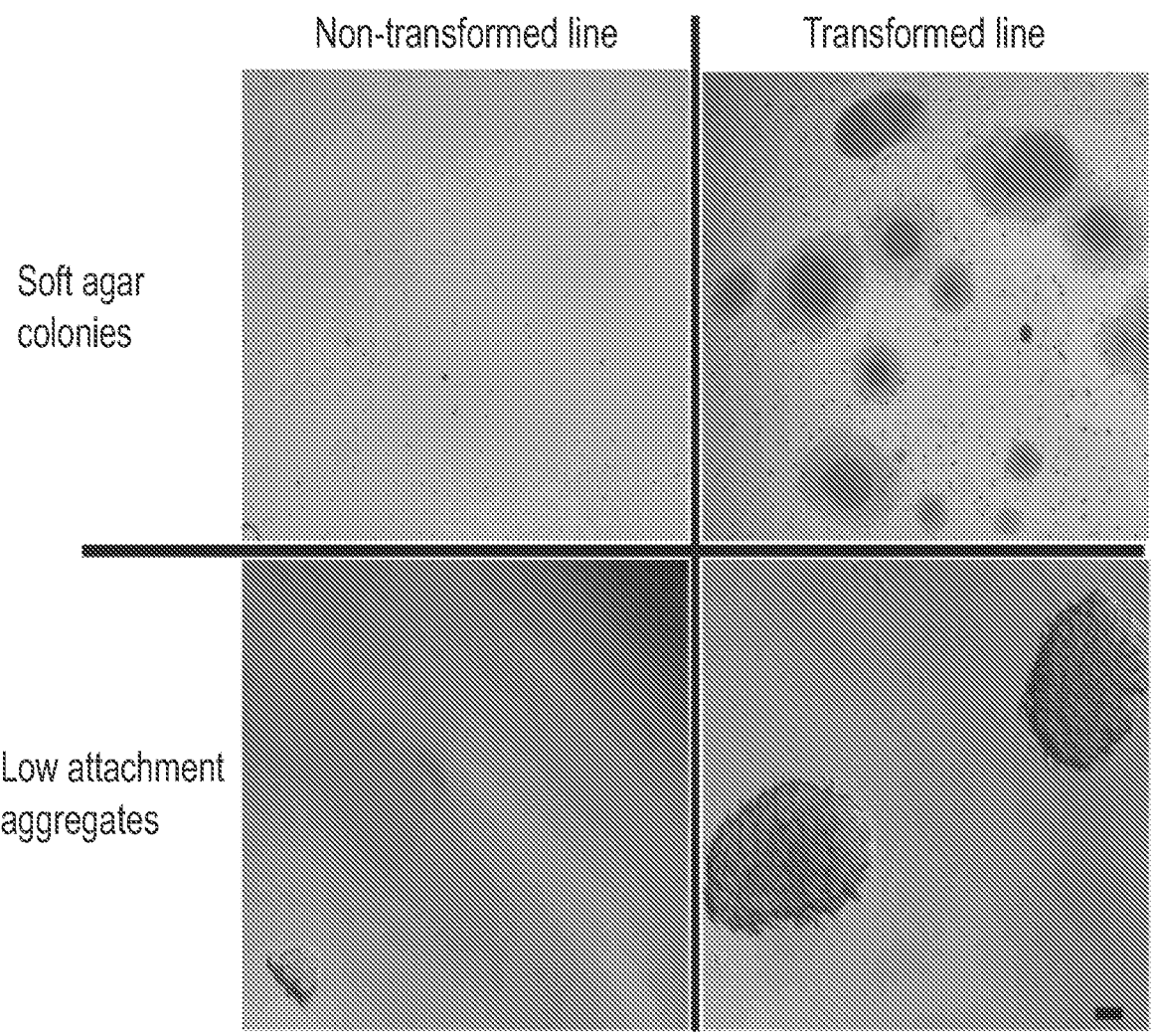
FIG. 7 is a set of digital images of phase contrast images of non-transformed (left) and transformed fibroblast cell lines (right) after 21-day growth in SA (upper panel) and 5 days in GILA (bottom panel). Scale bar—100 µm.

To examine whether GILA was comparable to the soft agar assay, soft agar assays were performed on the same cell lines. As expected, a large number of big colonies developed from transformed cells, while non-transformed cells generated very few small size colonies and mostly individual resting cells (FIG. 7). When transformation values of both assays were plotted, the linear correlation coefficient value is 0.68 (FIG. 1), which signifies a strong correlation, indicating that GILA and the standard soft-agar assay are essentially comparable assays for transformation.

The GILA Assay Specifically Measures Cellular Transformation.

Figure 2:
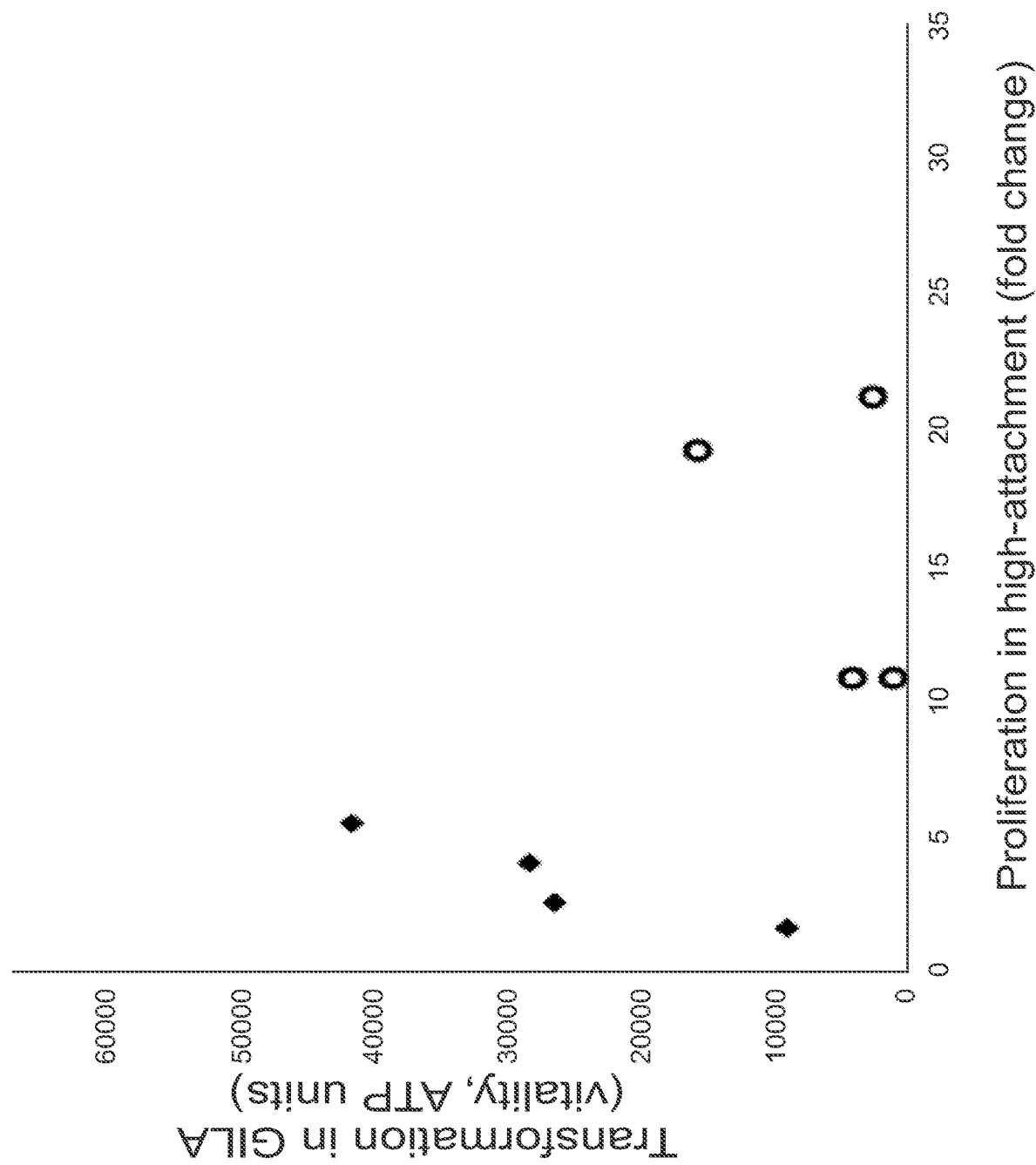
FIG. 2 is a graph showing that anchorage-dependent growth of normal and transformed cells is distinct from anchorage-independent growth in a GILA assay. Proliferation values of viable cells after 5 days of anchorage-dependent growth correlate poorly with those in low-attachment conditions ($R^2=0.12$). Non-transformed cell lines grow faster than transformed lines in high attachment conditions. Each experiment had three independent repeats. These observations indicate that GILA specifically measures oncogenic capacity independent from growth per se.

To confirm that growth in conditions of low attachment is a measure of transformation and not simply growth per se, the growth of cells as a monolayer on a traditional high-attachment surface was compared to three-dimensional growth in the GILA assay (FIG. 2). Proliferation rates on high attachment conditions correlate poorly with those on low-attachment conditions ($R^2$=0.12). In fact, with the exception of fibroblasts, non-transformed cells grow faster than transformed cells on high-attachment conditions, high-attachment conditions, the opposite situation from low-attachment conditions (FIG. 8). These observations indicate that GILA specifically measures of oncogenic capacity of transformed cell lines independently from the proliferation rate.

A GILA-Based Drug Screen in Transformed Fibroblasts Identifies Anti-Neoplastic Compounds Overlooked by a Conventional Screen.

Most high-throughput screens for small molecules or genes that have anti- or pro-tumorigenic roles are performed under standard growth conditions on high-attachment surfaces. As such, the candidates passing these screens may inhibit or enhance general proliferation but not necessarily have a specific effect on transformation or cancer cells. To identify drugs specifically inhibiting the oncogenic state of fibroblasts transformed with TERT, SV40 T-antigen, and H-RAS (Hahn W C, et al. (1999) Creation of human tumour cells with defined genetic elements. Nature 400:464-468.), GILA was used as a primary screen and growth on standard high-attachment plates as a counterscreen. Drugs specifically affecting the transformed state would inhibit anchorage-independent growth as assayed by GILA, but have little effect on high-attachment conditions.

Figure 3A:
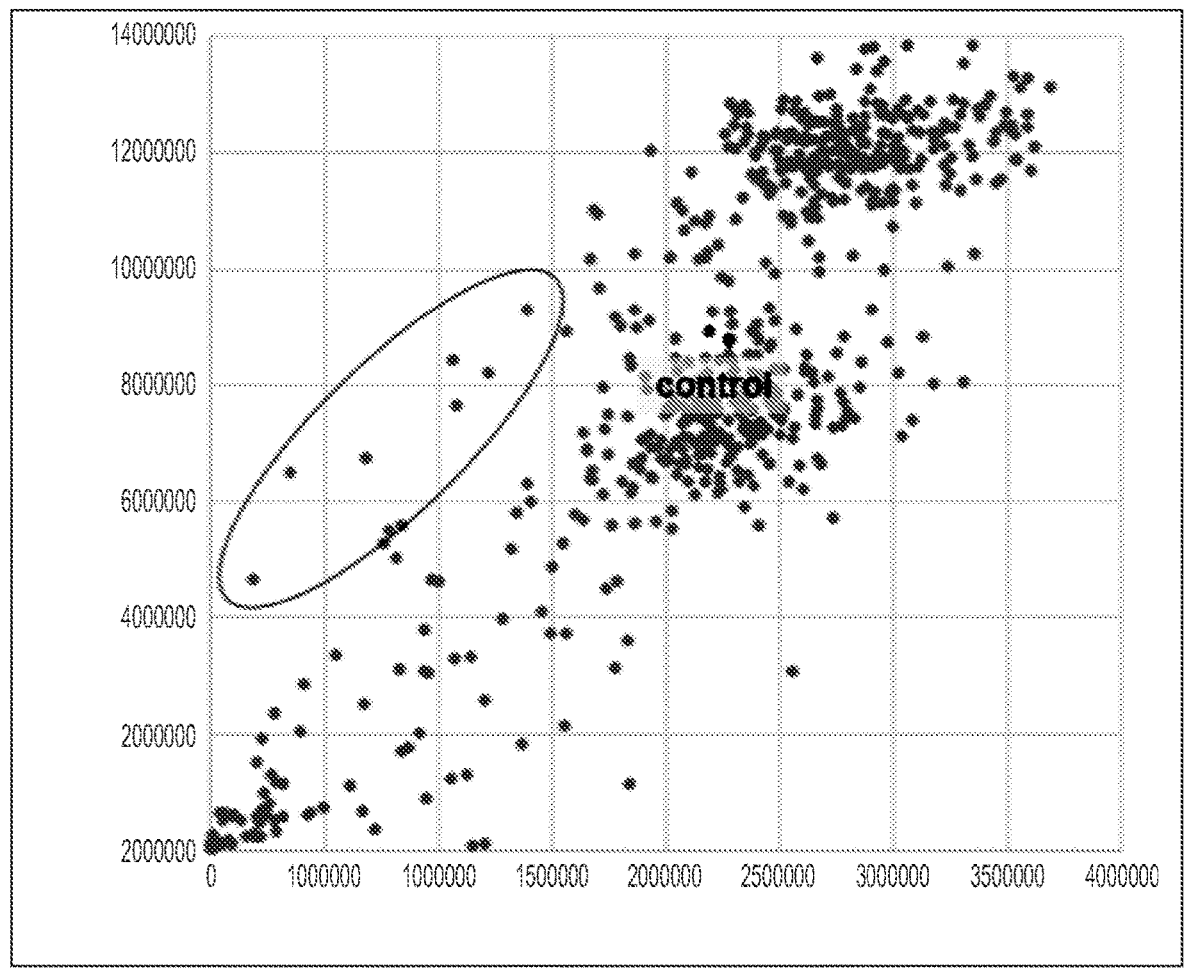
FIGS. 3A-3C is a set of graphs and digital images showing GILA for screening small molecules for antineoplastic activity.
Figure 3B:
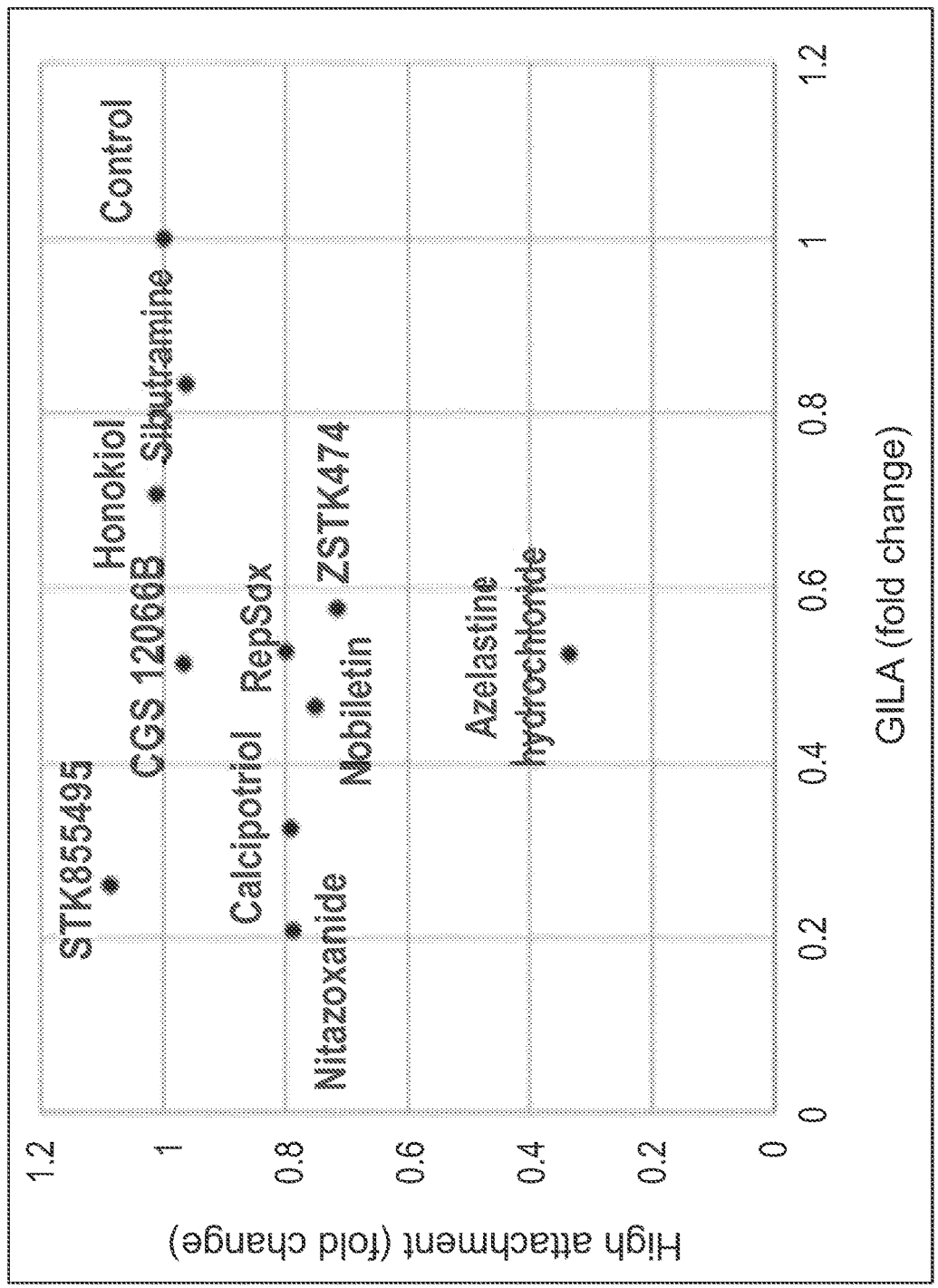
Figure 3C:
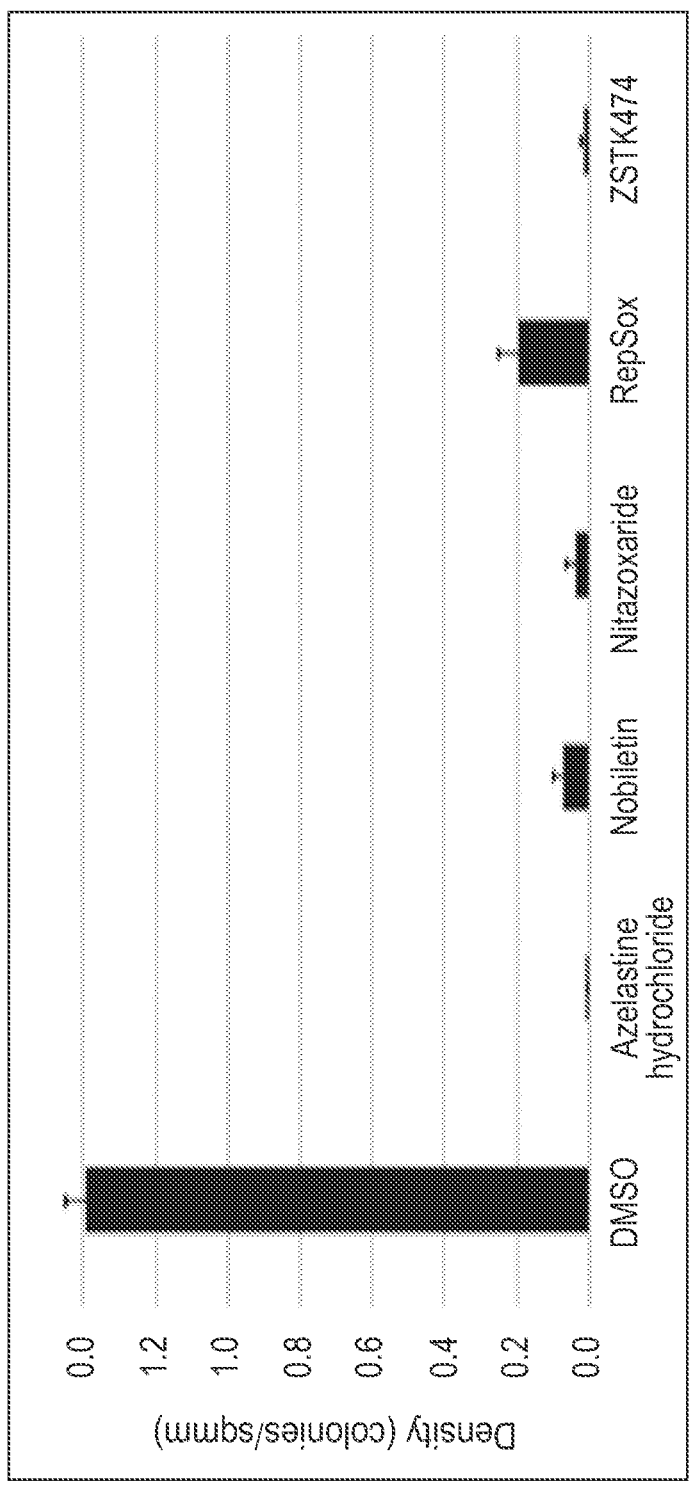

Among the 633 kinase inhibitors and FDA-approved drugs screened, we identified 10 drugs that significantly inhibit cell growth in the GILA assay, while having a less pronounced inhibitory effect on the high-attachment surface (FIGS. 3A, 9). These 10 compounds were subject to a validation (secondary) screen. 4 drugs inhibited cell growth exclusively in the GILA assay, 5 drugs preferentially inhibited growth in low attachment conditions will small inhibitory effects on high-attachment growth (~20% reduction), and one drug inhibited growth to comparable extents in high- and low-attachment conditions (~50% reduction). These drugs would probably have been ignored in a conventional screen for growth, but their ability to inhibit growth on low attachment surfaces (reduction of 20%-80% at the concentrations tested) make them interesting candidates with specific antineoplastic activity (FIG. 3B). As expected, the 5 candidate drugs tested inhibit colony formation in the soft-agar assay (FIG. 3C).

Drugs used for treatment of diabetes, atherosclerosis, and inflammatory disease often inhibit transformation and tumor growth, and these diseases have similarities in their 7 transcriptional signatures (Hirsch H A, et al. (2010) A transcriptional signature and common gene networks link cancer with lipid metabolism and diverse human diseases. Cancer Cell 17:348-361.). In this regard, five of the top hits from our drug screen have never been shown to play a role in cancer and hence might be interesting candidates to repurpose for cancer therapy. In contrast, three drugs (calcipotriol, sibutramine and nitazoxanide) have targets that affect pathways that overlap with cancer-related pathways (Amelio I, et al. (2014) DRUGSURV: a resource for repositioning of approved and experimental drugs in oncology based on patient survival information. Cell Death Dis. 5:e1051). For example, the anti-viral drug nitazoxanide suppresses IL-6 (Hong S K, et al. (2012) Nitazoxanide suppresses IL-6 production in LPS-stimulated mouse macrophages and TG-injected mice. Int. Immunopharmacol. 13:23-27), a cytokine frequently linked to carcinogenesis.

Patient-derived ovarian cancer cells are sensitive to FDA-approved drugs identified in the GILA-based screen. To test whether drugs identified and validated in the drug screen had anti-neoplastic activity in the context of human disease, we isolated fresh, ascites-derived ovarian cancer cells from 5 patients who had failed multiple lines of treatment (FIG. 10). Immediately after procurement, ascites samples were processed and 5000 cells per well were flow-sorted into 96-well microtiter plates with low or high-attachment surfaces containing 100 µl of growth medium per well. These ex-vivo cultures were treated individually with four FDA-approved drugs identified and validated in the drug screen (azelastine hydrochloride and nitazoxanide, RepSox or nobiletin) for 72 hours. Two compounds, azelastine and nitazoxanide, demonstrated inhibitory activity in the GILA assay (FIG. 4A), with a dose dependent response shown for azelastine hydrochloride (FIG. 4B). Interestingly, cancer cells from the various patients displayed differential sensitivity to these drugs. These results validate ex-vivo GILA-based drug screens as a potential tool for drug discovery and repurposing to individually treat cancer patients who have failed to respond to conventional treatment.

A Genome-Scale ORF Screen Identifies Genes that Specifically Increase Transformation.

GILA was used in a genetic screen for oncogenes by introducing a barcoded library of lentiviruses overexpressing protein-coding regions (18,000 clones representing 14,000 genes) into MCF-10A, a non-transformed breast cell line (Soule H D, et al. (1990) Isolation and characterization of a spontaneously immortalized human breast epithelial cell line, MCF10. Cancer Res. 50:6075-6086). Upon integration of the lentiviruses into the genome via puromycin selection, the resulting mixture of cells was grown for 5 days in flasks either with high-attachment or low attachment surfaces. Representation of individual expressed genes in resulting cell populations were determined via the barcodes. In principle, lentiviruses expressing oncogenes should yield preferential representation in the low-attachment vs. high-attachment populations.

Figure 5A:
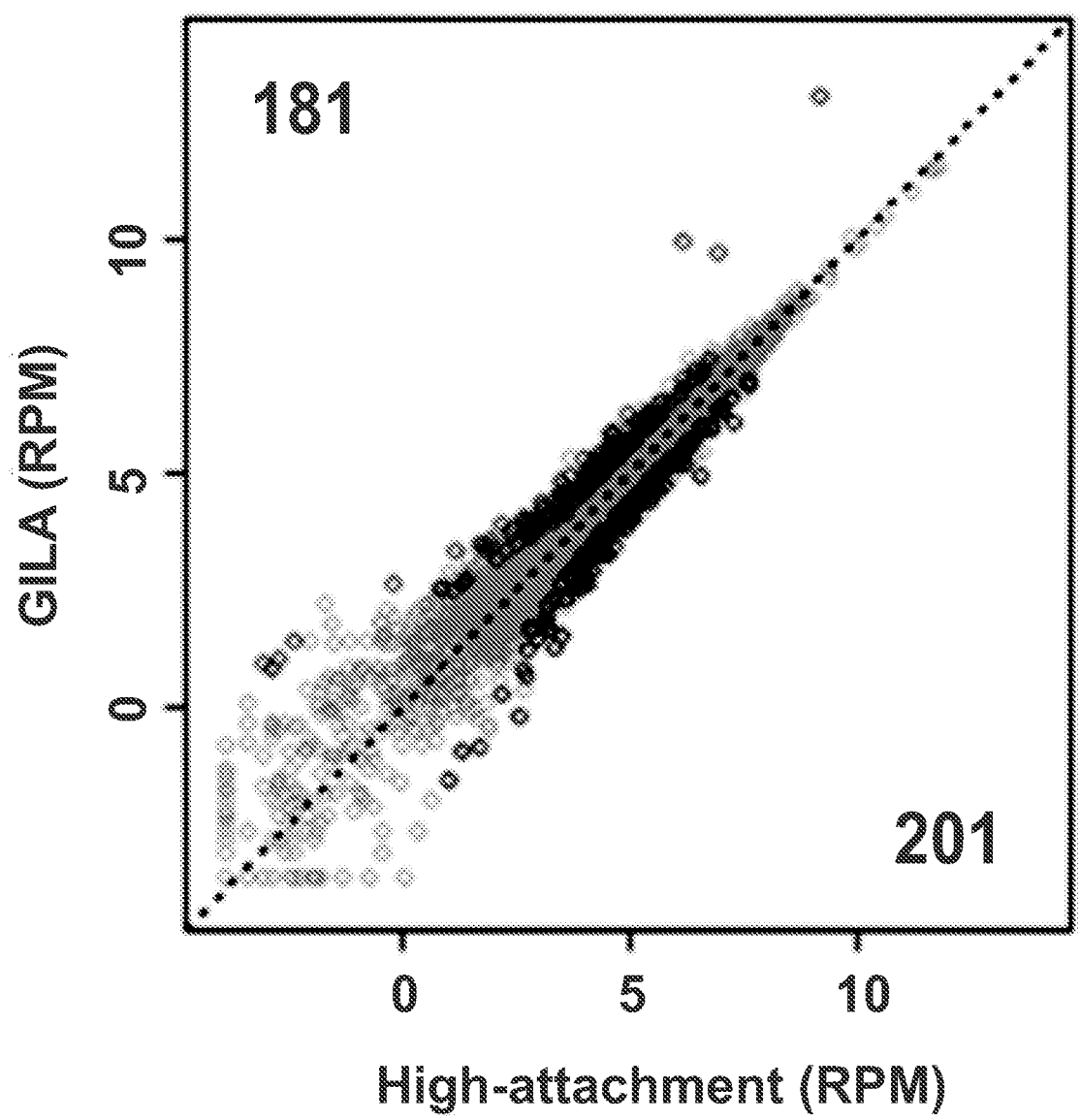
FIGS. 5A and 5B are a set of plots showing a genetic screen for ORFs with oncogenic role in MCF-10A cells.

Two observations validate both GILA and the genetic screen. First, the top hits are the well-known oncogenes H-Ras, K-Ras, and EGFR. Second, kinases, receptors, and signaling pathways linked to cancer are identified by gene-set enrichment analysis of the entire dataset based on rank-ordered barcode ratios from low:high attachment conditions (FIGS. 5A and 11). In contrast, no gene sets are enriched when the genes of the dataset are rank in inverse (high:low attachment) order.

Figure 5B:
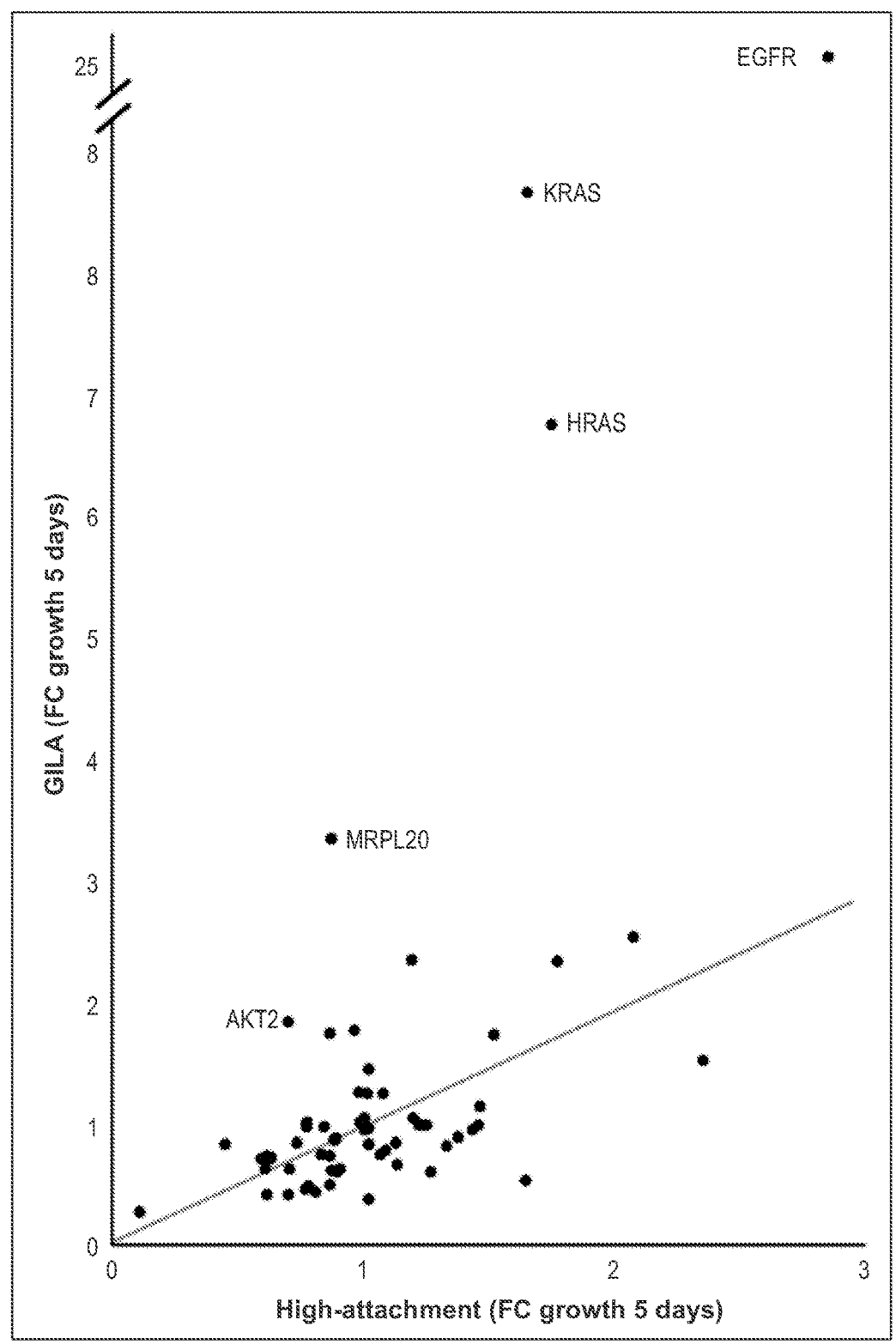

To individually examine the oncogenic effect of individual genes more directly, MCF-10A cells were infected individually with lentiviruses overexpressing 62 candidate genes from the genetic screen, and the resulting stable cell lines tested for growth in high- and low attachment conditions (FIG. 5B). As expected, cell lines overexpressing H-Ras, K-Ras, or EGFR grow much better in low—but not high-attachment conditions than the parental cell line, confirming their oncogenic properties. In addition, cells overexpressing MRPL20 or AKT2 grow preferentially in low-vs. high-attachment conditions (p-value<0.001; FIG. 12); a few other genes (MAP3K3, EIF4E, PPP1R8, and C3orf62) may behave similarly (p-values ~0.02). Although not previously characterized as an oncogene, MRPL20 expression levels are part of a 16-gene principle components predictive of breast cancer risk (Huang C-C, et al. (2013) Concurrent gene signatures for Han Chinese breast cancers. PloS one 8:e76421.). Although differences between growth in low vs. high attachment are modest for these genes, the results suggest that at least of some of them (and perhaps others implicated in the gene-set analysis) can make minor contributions to the oncogenic state. By analogy, deep sequencing on many cancer genomes reveals many cancer-promoting or cancer-suppressing genes that individually make a minor contribution.

Materials and Methods

Cell Culture.

The non-transformed breast cell line MCF-10A (Soule H D, et al. (1990) Isolation and characterization of a spontaneously immortalized human breast epithelial cell line, MCF10. Cancer Res. 50:6075-6086) was grown in DMEM/F12 medium supplemented with 5% donor horse serum, 20 ng/ml epidermal growth factor (EGF), 10 µg/ml insulin, 0.5 µg/ml hydrocortisone, 100 ng/ml cholera toxin, and antibiotics (penicillin/streptomycin) (Debnath J, Muthuswamy S K, & Brugge J S (2003) Morphogenesis and oncogenesis of MCF-10A mammary epithelial acini grown in three-dimensional basement membrane cultures. Methods 30:256-268). Other breast cell lines (T47D, MDA-MB-231 and MDA-MB-486) were grown in DMEM media, 10% FBS, and antibiotics. The three BJ fibroblast lines (EH, EL, ELR) were cultured in KO-DMEM media, 15% FBS, 16.5% Medium 199, 3.5 mM L-glutamine, and antibiotics (Hahn W C, et al. (1999) Creation of human tumour cells with defined genetic elements. Nature 400:464-468). Non-transformed WI-38 lung fibroblasts were grown in Eagle's MEM supplemented with 10% FBS and antibiotics. Not transformed (BPH1) and transformed (PC3) prostate cell lines were maintained in RPMI-1640 medium supplemented with 10% FBS and antibiotics (Lim J T, et al. (1999) Sulindac derivatives inhibit growth and induce apoptosis in human prostate cancer cell lines. Biochem. Pharmacol. 58:1097-1107). Three subcloned cell lines from human ovarian cancer primary cells were maintained in KO-DMEM media, 15% FBS, 16.5% Medium 199, 3.5 mM L-glutamine and antibiotics. SAA1 is a cell line with a low-grade transformation value, SAA2 is a mild-grade and SAA3 has the highest transformation value, as assessed in vitro and in vivo. All cells were grown in a 5% CO2-humidified incubator at 37° C.

Soft Agar Assays.

Cells (105/well) were mixed with 0.4% agarose in growth medium, plated on top of a solidified layer of 0.5% agarose in growth medium, in a 24-well plate, and fed every 3 days with growth medium. After 3 to 4 weeks, the colonies were dyed with Cristal Violet (0.01% solution), washed with PBS and imaged using a custom, automated plate imager with a digital camera (Olympus SP-350, Cam2Com) (Chait R, Shrestha S, Shah A K, Michel J B, & Kishony R (2010) A differential drug screen for compounds that select against antibiotic resistance. PloS one 5:e15179). A custom MATLAB program was developed to first detect each well in the plate, based on Canny edge detection and morphological post processing. Colonies were detected within each well using the wavelet transform-based detection algorithm (Olivo-Marin (2002) Extraction of spots in biological images using multiscale products. Pattern Recognit. 35:1989-1996). Image pixel sizes were calibrated by relating user input of the physical size of the plate to the detected spacing between wells in image space. This calibration was used to calculate colony area in square microns and to calculate equivalent radii. This produced both net colony density for each well.

GILA Assay and Drug Screens.

Transformed fibroblast cells were maintained as subconfluent monolayers, trypsinized, and seeded in 96-well plates (for analytical assays, FIG. 14) or in 384-well white plates (for screens, FIG. 3). The cell concentration was optimized to 1000 cells/well in 100 µl medium (for 96-well plate) or 50 cells/well in 30 µl growth medium (for 384-well plate). Two types of plates were used in the screens: high-attachment conditions (Corning, 3704) and Ultra Low-attachment (Sumitomo, PrimeSurface384U). Cells were seeded automatically using the liquid rapid dispenser Metrix WellMate (Thermo). Two small molecule libraries (NIH Clinical Collection 1-2013 and Kinase Inhibitor Focused Library) were transferred to each microplate, at 100 nl drug per well, to final concentration of 30 µM or 10 µM, respectively, by using the robotic transfer system (Seiko Epson) and pin array (V&P). Controls were added by multichannel pipette. After 5 days of incubation at 37° C. in 5% $CO_2$, the cells were assayed for ATP content. Each plate had a duplicate and the entire screen was repeated two times. The secondary screen was conducted similarly, except that an HP D300 Digital Liquid Dispenser and T8 dispenseheads (HP) was used to add 4 different concentrations of small molecules to the cells.

Cell Viability Assay.

Cell viability was measured with the CellTiter-Glo (Promega) luminescent assay, using the EnVision Plate Reader (PerkinElmer) or the SpectraMax M5 Multi-Mode Microplate Reader (Molecular Devices). For high-attachment growth, tissue culture-treated 96-well clear plates (#3997, Corning) were used, while for the GILA assay low attachment surface plates (#3474, Corning) of 96-well clear plates were used for 3 to 5 days. Later the cells were moved to 96-Well Solid White Polystyrene Microplate (#3362, 14 Corning) for reading luminescence signal. To avoid bleeding of luminescence between the wells, every other well left empty in the solid white microplate. 30 µl of CTG reagent was used for 384-well microplates, and 100 µl for 96-well microplates. The cells were moderately shaken for 5 minutes in the reagent, followed by incubation for 20 minutes to ensure cell lysis. No background signal was detected from wells containing only culture medium.

Identification of hits from the drug screen.

Crosstalk corrected values from EnVision reader were used to normalize the luminescence from each wells. Negative control values were used to calculate the Z score for each well in each replicate, with the formula ((Luminescence−average of negative control)/standard deviation of negative control. Z score values were graded strong (S), moderate (M) or weak (W), where −5>S, −5>M>−4.5 and −4.5>W>−3.2. To be considered a hit, a drug had to score positive in one of replicates on the low-attachment plates and to score negative in the high-attachment condition. Finally, the selected hits had to have a ratio of luminesce (low/high attachment)<0.25.

Patient Samples.

Under an institutional review board approved protocol, freshly discarded ascites from patients with advanced stage ovarian cancers was collected from 5 individuals. Ascites fluid was immediately transferred on ice for further processing. Samples were spun down and red blood cells were removed with hypotonic lysis using ACK lysing buffer (Life Technologies). Cells were filtered through a 40 μm mesh and washed in PBS with 2% FBS and subjected to staining for FACS.

Flow-Cytometry.

Cells were prepared per standard protocols, stained with Calcein-AM, CD45-FITC, EPCAM-PE and CD24-PE/Cy7 and incubated for 20 minutes on ice. Cells were washed with FBS with 2% FBS prior to flow-sorting. After doublet discrimination and compensation for spectral overlap, single, viable cells, negative for CD45 and positive for EPCAM and CD24 were flow-sorted into wells (96 well plates) prepared with growth 15 medium. Samples were sorted on a BD FACSAria SORP and analyzed using BD FACSDiva Software (BD Biosciences).

Oncogenic ORF Screen.

MCF-10A cells were infected with a library of barcoded ORFs(20) at a low (<1) multiplicity, with an average of 1000 cells per ORF clone, and infected cells were selected with puromycin for 5 days. Genomic DNA samples were taken from the resulting cells and noted as early time point (ETP). These cells were then seeded into two types of flasks with different surfaces-traditional high attachment (430641, Corning, USA) or ultra-low attachment (3814, Corning, USA) and grown for an additional 5 days. Following genomic DNA preparation, PCR was performed to amplify the barcode, followed by Illumina sequencing of the product to determine the relative abundance of each ORF in the different attachment conditions. Genes of interest were identified as having significantly different representation (by sequence reads) from libraries from the low-attachment condition as opposed to the high-attachment condition.

A secondary validation screen was performed on 62 genes selected from the primary screen by using the following criteria: values of GILA over high-attachment growth >1.5 fold; expression values consistently up-regulated >1.2 fold and Poisson test p-value <1E-4 (~Benjamin Hochberg corrected FDR 0.01). We furthermore required the ORF encoding genes should be well expressed in breast tissues, using RNA-seq data from the Cancer Genome Atlas database (Cancer Gene Atlas Network (2012) Comprehensive molecular portraits of human breast tumours. Nature 490: 61-70.). For each gene to be tested, the appropriate lentivirus expressing this gene was infected into MCF-10A cells, and infected cells were selected with puromycin for 5 days. The resulting cells were tested in 96-well low- and high-attachment plates and assessed by the cell viability assay described above. Statistical significance for oncogenic behavior of individual genes was determined with respect to the normalized distribution of tested targets centered on a trimmed mean, a conservative approach.

Example 2

This example describes a method for the assessment of tumorigenicity of cell, in vitro and ex vivo, and the steps towards optimizing the method for individual applications. This protocol presents one main method with three optional applications. The main method is GILA assay using cell lines, and an optional method is GILA assay using primary patient-derived cells. The two additional applications described in this protocol are pharmacological and genetic perturbations. While the unit describes the pharmacological approach for both cultured and patient derived-cells cells, the genetic screen has been used only for cultured cells. This protocol uses appropriate cell number and reagent volume for 96-well plates; some adjustment will be necessary if using another format.

Materials List

Solutions and reagents: Cell line, growth medium (DMEM, FCS, antibiotics), trypsin, PBS, cell counter device/hemocytometer, ATP quantification reagent (CellTiter-Glo kit, CTC, Promega), plate reader for luminescence, aluminum cover foil and roller, dATP.

Special equipment: 384-well plates; traditions (high-attachment surfaces) Corning; #3704 and Ultra Low-attachment (ULA) Sumitomo; Prime Surface 384U; 96-well solid whit polystyrene plate (3362; Corning).

For pharmacological screens: liquid rapid dispenser or a digital liquid dispenser, drug transfer system and/or pin array for liquid transfer.

Basic Protocol Steps and Annotations

1. Choose cell lines that fit the aims of experiment. The cell type tested in this assay is limited to adherent lines; these will pass the low-attachment growth test, if they are transformed. Optional: ex vivo culturing of patient-derived tumor cells may be used in addition to or instead of cultured cell line.

2. Choose a counterpart line to test in parallel. For example, if the aim is to screen drugs for antitumor activity and the tested line is a Src-transformed breast cell line, it would be appropriate to compare to a wild-type cell line that lacks Src expression. Thereby a baseline viability can be used to define the efficiency of a drug on transformed cells and the toxicity toward non-transformed cells. This is useful to establish a "therapeutic window" for an individual experimental design. Alternatively, only one cell type can be tested and the treatments will be compared to the control group, which are exposed to mock treatment (e.g. DMSO/water) or the same treatment on a standard platform (e.g. regular/high attachment surface). Throughout this protocol, follow traditional culturing procedures (e.g. detachment, seeding and recovery time from seeding) relevant to your chosen cells and as previously defined by the user.

3. Grow about 5 million of the choses cells in a traditional tissue culture dish. In this example embodiment cells are grown prior to implementing the GILA assay; use full growth medium that is suitable to the cells and use traditional dishes for cell culturing. It is recommended to start the assay with a few million cells and seed cells accordingly a few days before using the GILA assay.

4. Prepare multiwall plates. Prepare plates that will not allow the cells to adhere to surfaces, by treating the wells with a polymer that prevents cellular attachment (see critical parameters). These plates are also commercially available. Set pre-coated plates for ultra-low attachment alongside traditional plates (with high-attachment surfaces).

5. Wash cells with warm 1×PBS.

6. Detach the cells by using warm trypsin (precise concentration and duration is variable across cell lines).

7. Add fresh medium and count the cells.

8. Seed 500-5000 cells per well in 4-5 replicates into two types of 96-well plates; with low- and high-attachment surfaces. See FIG. 14. Use the same growth medium as before (step 3). It is recommended to optimize the density-dependent viability of cells before this step, for every cell type (see critical parameters section). Consider the volume of medium in a well, taking into account that an additional reagent will be added to the well at a later step. For example, in a 96-well plate the maximal volume is about 225 pit per well. Therefore, it would be ideal to seed the cells in 100 pit medium in order to allow the addition of 100 pit of cell lysis reagent without overflowing the well. Seed the same cells also into traditional, high-attachment surface plates. Optionally, perform gene perturbation. Seed cells into a traditional high-attachment dish and infect the cells with genetic material for RNAi or over-expression.

9. Incubate cells in 37° C., 5% $CO_2$ incubator for 3-5 days. 24 hours after seeding, confirm that the cells have settled and are growing. Make certain that cells grown on high-attachment surfaces are not confluent.

10. Manipulate the cells—perform drug screen or continue genetic perturbation. Usually after 24 hours from seeding the cells, it would be appropriate to treat the cells with drugs or small molecules. A day after cell seeding the cells will settle in the wells and start to propagate. Adding drugs to the growth medium at this time should affect cellular growth and viability. Also, cells that went through genetic perturbations could be moved to dishes with low- and high-attachment surfaces. These cells may grow a few days in these dishes.

11. Inspect the cells for growth and microbial contamination. Using a light microscope to observe or image the wells for sphere/aggregates growth and for detection of contaminants, especially towards the end of the treatment. For opaque plates, move the medium to a microscope slide or a clear plate for visualization. Optional addition—seal and freeze plates at −80° C. on the last day for later measurement of ATP (see support protocol).

Lyse Cells and Measure Cellular Viability.

12. Lyse cells by adding 100 µl of CTG reagent, into each well (96-well plate). The cells should be lysed inside the well. Add CTG on top of cells and medium.

13. Cover the plate with aluminum foil and orbital-shake the plate at 100 rpm for 2 minutes at room temperature. Make sure to shake at a moderate speed and avoid splashing onto the foil cover.

14. Stop shaking and incubate the plate for 10 minutes at room temperature.

15. Using a 200 µl multi-channel pipette, move the CTG-cells-medium mix (~200 µl) from each well to new well in a 96-well opaque plate. Move the replicates of lysed cells into wells and leave at least one well between each condition, in order to prevent leaking of signal from a neighboring well. Optional—Use opaque plates at step 8 and skip this step-move directly to step 16.

16. Move opaque plates to reader and read luminescence. Instrument settings depend on the reader manufacturer.

17. Analyze ATP levels as a proxy for cellular viability.

Alternate Protocol 1—Ex Vivo GILA Assay for Primary Patient-Derived Tumor Cells

As described at step 1 in the Basic protocol, choosing a cellular system is an important step in this assay. Primary cells from a patient are a very useful model in which GILA assay is used to examine drug sensitivities of ex vivo tumor culture. Although it is beyond the scope of this unit to describe in detail the generation of single-cell solutions suitable for ex vivo cultures from various clinical specimens, we provide an example: To assay tumor cells from malignant effusions, for example peritoneal fluid (ascites) derived from patients with ovarian cancer or other cancer, follow these steps:

1. Spin down the malignant fluid at 580 g for 5 minutes at 4° C.
2. Perform red blood cell lysis using hypotonic lysis buffer (such as ACK) and incubate the sample on ice for 2 minutes.
3. Filter the cells through a 70 µm mesh.
4. Resuspend the resulting cell pellet in PBS with 2% FCS.
5. Prepare for fluorescence-activated cytometry sorting using highly specific markers, in this case—label with EPCAM and CD24.
6. Seed 2500-5000 cells per well (of 96-well plate) using the flow-cytometer or by serial dilution (Rotem et al., 2015).

One significant challenge is determining an ideal growth medium, which supports growth over time (a few days).

Materials
1. ACK buffer (Life technologies)
2. 70 µm filter (Miltenyi Biotec)
3. Fluorescent-labeled antibodies (Miltenyi Biotec)
4. Fluorescence-activated cytometry sorter (BD)

Genetic Perturbation Followed by GILA Assay

Figure 14:
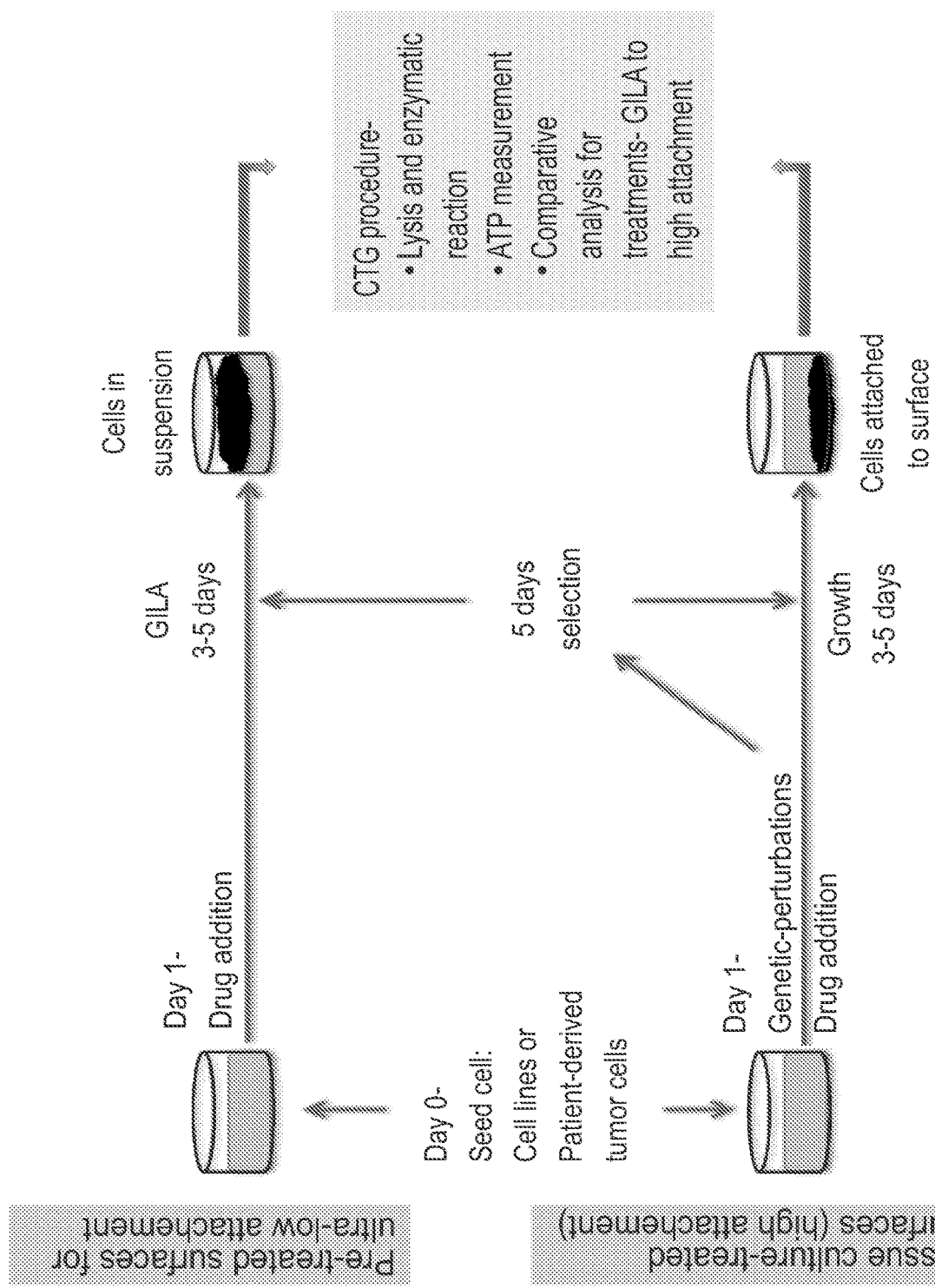
FIG. 14 is a schematic overview of an assay for assessing cell viability using a GILA assay, in accordance with certain example embodiments.

As previously mentioned in step 8 of the Basic protocol, the GILA assay might serve as a selection method for genetic perturbations like RNAi, CRISPR or ORF expression (FIG. 14, bottom panel). The latter was implemented by us (Rotem et al., 2015) and can be used as an example for genetic screens.

Pooled screen—
1. Prior to the actual screen, optimize the density of cells and the duration of the assay (see critical parameters). This should be done for each dish/flask type that will be used in the screen.
2. Infect adherent cells with a library of barcoded ORFs, with an average of 1,000 cells per ORF clone. Keep this ratio of 1000 cell/ORF through all following step, to ensure a sufficient and constant cell number for a complete representation of the library. For example— for a library of 18,000 ORFs keep a minimum number of 18,000,000 cells, especially after splitting cells.
3. Select for ORF-expressing cells with antibiotics for 5 days.
4. Sample genomic DNA from the resulting cells, marking as early time point. This sample will be used to calculate cellular growth rate after 5 days. Document cell concentration (number of cells/ml) of this sample for an accurate calculation of growth rate.
5. Seed these cells into two types of flasks with different surfaces—traditional high attachment or ultra low attachment. Preferably, seed an equal amount of cells in each attachment conditions. If the cells grow in flasks with ventilation cap, avoid using a large volume of medium that could spill through the cap and contaminate the cells.
6. Grow cells for 5 days. During this time spin down floating spheres/cell aggregates and move to a larger ULA dish/flask with fresh growth medium. This might require optimization of centrifugation velocity in order to keep the spheres/cell aggregates intact.
7. Isolate genomic DNA from the cells using a commercial kit and follow the next steps. Count the cells and use the same cell concentration as documented at the early time point (step 4).
   A. Amplify the ORF-barcodes by PCR, using vector-specific primers.
   B. Sequence the product using Illumina sequencing primer to determine the relative abundance of each ORF in the different attachment conditions.
   C. Describe ORF representation as "day 5" value compared to "early time point" value. This should give a 5-day growth ratio for each attachment condition.

D. Identify genes of interest as those with over-representation at the low-attachment condition as compared to the high-attachment condition.

Arrayed screen—Use this screen to test individual ORFs or hit list after the pooled screen.
1. Infect each gene separately into cells, similarly to the pooled screen (steps 1-2).
2. Select for ORF-expressing cells with antibiotics for 5 day.
3. Sample each of the ORF-expressing cells and measure cellular viability. Mark these values as early time points. Measure viability from the same cell number for all of the ORF-expressing cells, recommended range is 700-2000 cells. Document this cell number and use the same cell number at the next step (step 4).
4. Move resulting cells to 96-well low- and high-attachment plates.
5. Grow cells for 5 days. Cells with different ORFs might grow at different rates, it is recommended to monitor cellular growth by visualization. If certain cells overgrow to full confluence, repeat step 3 with less cells as before in order to avoid overgrown cells.
6. Assess cellular viability by CTG as described before; include uninfected cells as control group. For non-transformed cells you might expect to see cells growing on high attachment surfaces while on low attachment surfaces the cells die. Transformed cells will grow on both surfaces.
7. Identify oncogenic genes as those with higher representation at the low-attachment condition as compared to the high-attachment condition. Uninfected cells might be used to normalize viability values.

Materials
1. Flask with a traditional high attachment surface (430641; Corning).
2. Flask with an ultra-low attachment surface (3814; Corning).
3. Library of ORFs or any other gene perturbation method.
4. Infection reagents.
5. Library preparation kits and/or primers to sequence barcodes (Illumina).

BACKGROUND INFORMATION

Determining cellular growth in three-dimensional models is a highly relevant technique for in vivo transformation-related studies (Howes et al., 2014; Imamura et al., 2015). When compared to the classical growth of cells on plastic surfaces, three-dimensional models should be more similar to the physiological conditions, especially for cellular growth and tumorigenesis (Folkman and Moscona, 1978; Tanner and Gottesman, 2015). Soft agar has been the gold-standard three-dimensional technique for 50 years (MacPherson and Montagnier, 1964) and reflects well all the known characteristics of cancer cells, when compared to non-cancer cells. Other methods have been developed, each conveying specific advantages and disadvantages (Howes et al., 2014), yet the GILA method offers most of advantages over other methods and preserves the advantages of the soft agar assay. The GILA protocol described here aims at screening cells for drugs and genes in a transformation-specific method. One of the promising applications of GILA is the ability to test not only transformed cell lines, but to examine drug sensitivities of patient-derived ex vivo cultures. This is of particular interest in cancer types with defined genomic drivers, such as BRAF in melanoma or EGFR in non-small cell lung cancer, where mutations predict response to targeted inhibitors. These cells invariably develop treatment resistance through acquisition of additional mutations, pathway reactivation or a bypass pathway. Drug discovery in this scenario is a major endeavor and has tremendous impact on clinical patient care. Previous efforts at screening drugs to overcome treatment resistance have been carried out in two-dimensional cell cultures and the in vitro efficacy does not correlate strongly with in vivo activities (Imamura et al., 2015). Therefore, screenings of 3D ex vivo cultures, which more closely resemble the tumor and its microenvironment, may prove more predictive of the in vivo responses. While pharmacological perturbation is imminently applicable, success of genome editing approaches in primary patient derived ex vivo cultures remain challenging.

A. Critical Parameters

Patient-Derived Tumor Cells

The GILA assay is a relatively rapid method that does not necessarily require medium change or a special medium to maintain transformed cells. Yet, ex vivo assays for patient-derived cells, dependent on the origin of the tumor, might involve cells that grow very slowly or undergo senescence within days or weeks. It is critical to understand the unique culture requirements of ex vivo cells, for example the need to add growth factors, such as EGF or bFGF, and supplements such as B27.

Cell Density and Growth Duration

Figure 15A:
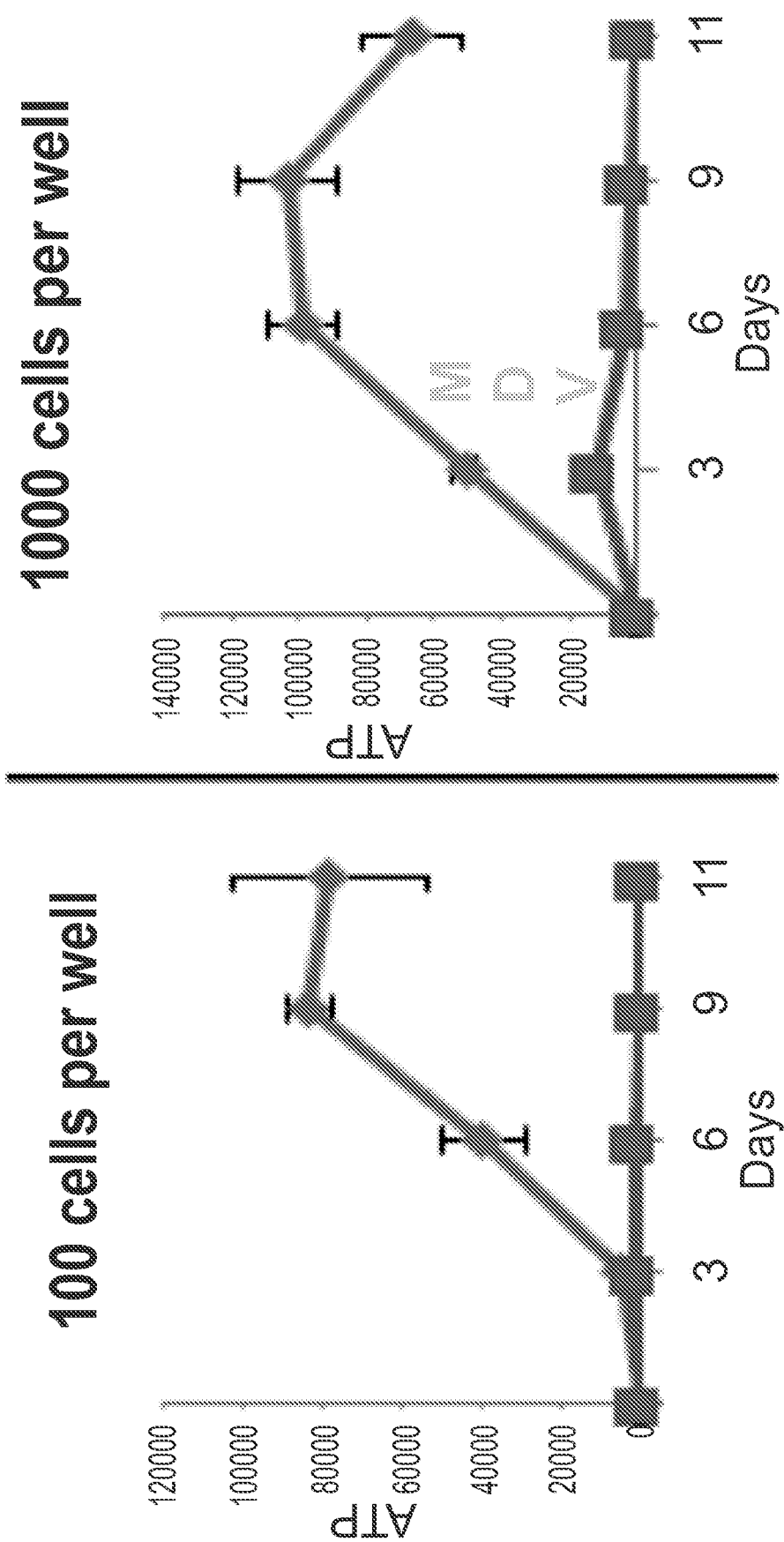
FIG. 15 is a series of graphs demonstrating the effect of keeping the same cell concentration but extending the duration of the experiment had on growth of cells in low-attachment conditions.
Figure 15B:
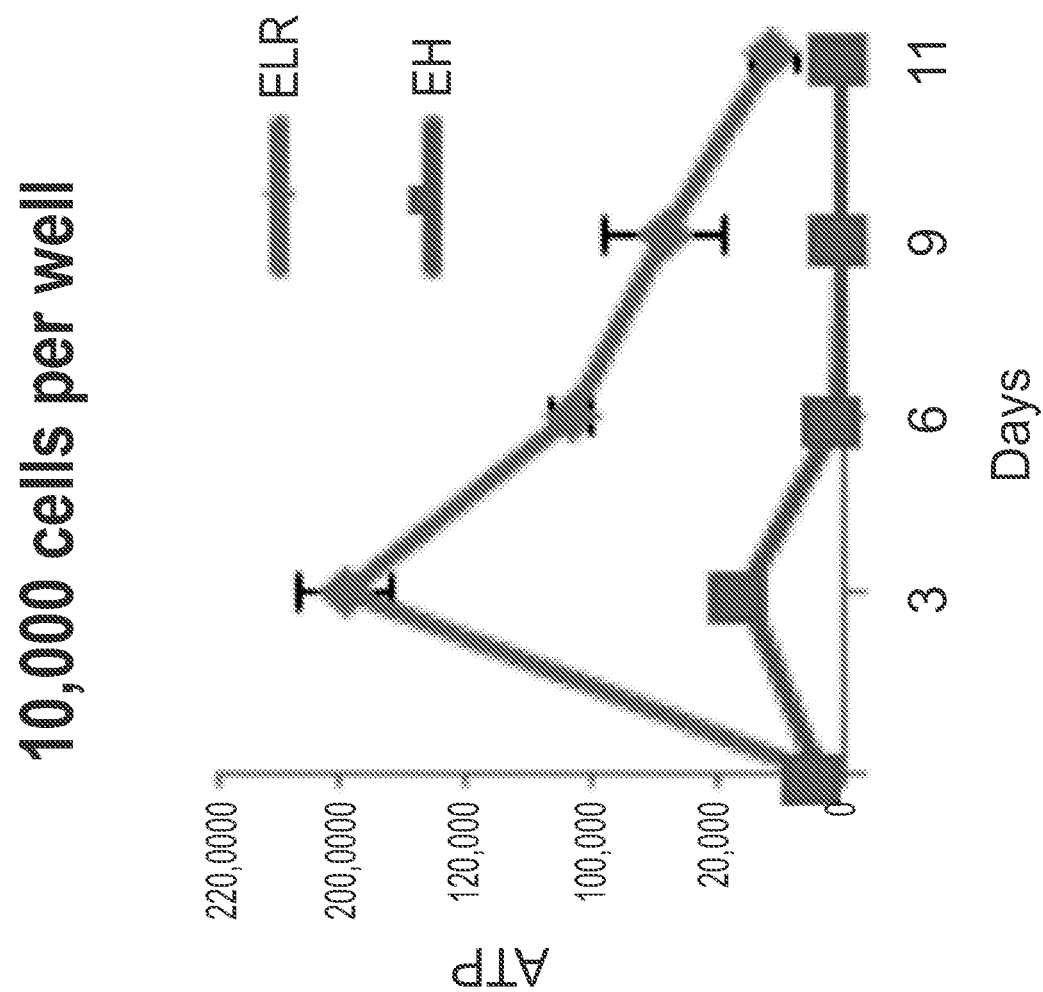

Important parameters are the concentration of seeded cells in each well and the duration of the assay. At the onset of an experiment it is essential to determine the ideal cell-number range, similar to any in vitro cellular assay. Yet, unlike traditional attachment conditions for adherent cells (on surfaces that allow cell attachment) cells that are grown on low attachment surfaces cannot be detected properly solely by visualization. While adhering cells propagate to maximal confluence followed by contact inhibition and cell death (Ozturk, 1996) (which can be easily observed visually), cells in low attachment grow into aggregates (Movie 1), which makes it hard to distinguish cellular propagation from overgrowth and cell death, simply by visualization. Also, once the cells grow as an aggregate it is very hard to disaggregate them to individual cells. To uncover the ideal cell-number range for a standard logarithmic growth of cells in low attachment conditions, it is necessary to find a proxy method for cellular growth, other than counting cell numbers. For that matter it is very useful to use methods that indicate cell number for a given growth area or volume (i.e. a well) by measuring metabolites, cellular components or any other value that is a direct outcome of cell density. One widely used method is to lyse the cells and measure cellular ATP, which is in correlation to cell viability (FIG. 15). Other proxy methods can be used instead of ATP measurement, yet we found that this approach is ideal for high throughput screens. We found that 500-5000 cells per well is good range for 96-well plates (in 100 µl medium) for many of the tested lines. The same was found for 384-well plates, with 50 cells in a single well (in 30 µl medium). After finding the ideal cell number to seed in each well, it is necessary to define an ideal time frame for the experiment and ATP assessment should help to determine the duration of the experiment. As demonstrated in FIG. 15, keeping the same cell concentration but extending the time of experiment might influence growth of cells in low-attachment conditions. In our hands two isogenic cell lines were used to optimize conditions for GILA; one line was transformed and the other line was non-transformed (Hahn et al., 1999). For example, the 100 transformed cells (ELR) that were seeded in a well needed 9 days to reach maximal growth before switching to their death phase, while 10,000 transformed cells reached death phase much quicker due to higher metabolic demands and a faster decrease in the pH (FIG. 15). Importantly, since the cells grow in suspension, one would like to minimize medium handling and simply leave the cellular aggregates in the same medium that the cells were seeded into. Therefore we would like to use enough cells to perform short experiment. We found that the ideal time range to perform this assay is 3 to 5 days, a time range which allows detecting changes in cellular viability due solely to the experimental treatments.

In addition, as shown in FIG. 15, it would be helpful to choose a cell line and to find a counterpart line to test in parallel. For example, if the aim is to screen drugs for anti-tumor activity and the tested line is Src-transformed breast cell line, it would be appropriate to compare to wild-type line that lacks Src expression. This way a basal line of viability will be used to define the efficiency of a drug on transformed cells and the toxicity towards non-transformed cells.

Multiwell Plates with Low Attachment Surfaces

Reduced attachment of cells to the surface of the well is a critical parameter in this assay and can be achieved by coating the wells, usually with a negatively charged polymer that prevents cell adhesion. PolyHEMA is a non-toxic and biocompatible polymer that is used for many biological applications (Phung et al., 2011; Yasumasa et al., 2013). Although polyHEMA coating might be a standard lab procedure, we found that for high throughput process it is better to use commercially available, pre-coated plates to reduce variability. Ultra-low attachment plates are available from several vendors like Corning, Sumitomo and others.

Another main parameter in any screen or high throughput procedure is the experimental setup, and here especially, the multi-well plates. When luminescence is the experimental outcome—the cells should grow in a plate that is compatible for luminescence signal reading. A clear plate, for example, is not appropriate for this technique. The best choice would be a white or opaque plate that will host the cells from the start to the end of the experiment. Alternatively, the experiment can be executed in two steps, with clear plates in the first step (for cell growth and manipulation) and in the second step, when the cells are moved to opaque plates; for CTG reaction and signal reading. Importantly, the outer wells of a plate should remain cell-free and be filled with PBS and not to be used for the actual measurements to avoid potential edge effects. This minimizes the available wells to 60 wells (for a 96-well plate) yet it is recommended for obtaining reliable results.

Lastly, culturing the cells in high-attachment conditions concurrently to GILA is a helpful comparative parameter. High-attachment surface plates will serve both as a positive control and as an independent condition in the experiment. For a first time use of GILA method it is helpful to observe cellular viability in the traditional growth on high attachment surfaces, in case the viability in GILA was compromised. Also, GILA aims to measure viability under anchorage-independent growth (as one of transformation bench marker), which is more specific for cancer models—a different growth trend in high-attachment will highlight the importance of the tested gene/drug to transformation, for example. Surprisingly, transformed cells were found to grow slowly on high-attachment surfaces as compared to their non-transformed counterpart cells from the same tissue (Rotem et al., 2015). Also, many informative reagents were overlooked due to minimal effect shown on high-attachment surfaces, yet these reagents were largely effective in low-attachment conditions (Rotem et al., 2015).

Viability Assessment

Measuring ATP levels as a surrogate for cellular viability—luminescence signals reflect the degree of cellular viability after genetic/pharmacological treatment, yet with every luminescence reading there is also background signal. If the reader is not already set to minimize the background signal, this should be done using wells filled with medium only. This should define the minimal viability value in the experiments and should be deducted from all the values in the experiment. The maximal values are usually from the control groups: DMSO or water-treated cells. Yet, some experiments involve over-expression of oncogenic genes (Rotem et al., 2015) or inhibition of tumor suppressors, which might result in higher viability than the control group. In these scenarios it is recommended to use the cells with the maximal value to set to minimum the bleeding of signals between two neighbor wells. Finally, the effect of a drug or genetic perturbation on viability might be presented as changes in viability of treated cells as compared to the control group or as compared to non-transformed cell line.

Figure 16:
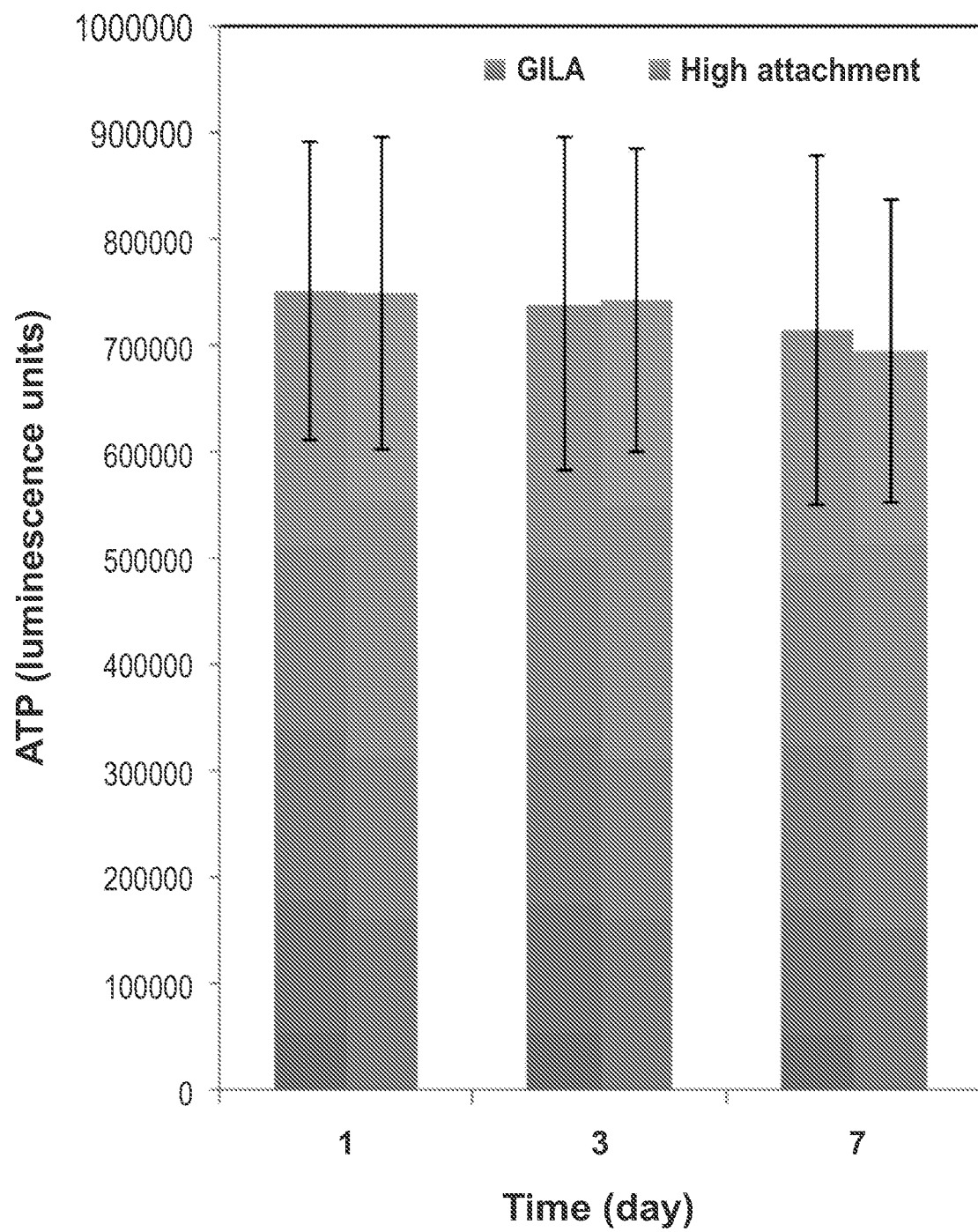
FIG. 16. is a graph showing similar ATP levels measured in frozen samples. Equal molarities of dATP were frozen at −80° C. for 1, 3, and 7 days inside plates with ULA or high attachment surfaces. ATP levels were measured at the same time for all the samples using fresh CTG reagent.

As luminescence reading is an end-point step in the assay, it should be done with the same settings throughout the experiment, to minimize technical effects. To ensure equal processing of cells from different time points in the experiment it is recommended to read luminescence at once. The following steps can be taken to achieve this; the cells should be seeded separately in one plate for each time point. For example: one plate will host cells for one-day growth and a separate plate for five-days growth duration. The plates should be sealed with aluminum cover foil at the end-point day (at day 1 and at day 5, respectively and individually) and should be stored in −80° C. freezer until the time that all plates will be treated with CTG reagent and immediately will be taken to luminescence reader. Before freezing, ATP in different molarities might be added to empty wells in each plate, to ensure similar treatment (FIG. 16).

B. Troubleshooting

1. Inconsistency in ATP levels within replicates—if for each treatment there are 4 or 5 repeats and the repeats yield different viability levels, there might be a few reasons for this;
   a. Incomplete trypsinization, caused the cells to detached in patches and to be seeded not as single cells in suspension. Ensure complete trypsinization before seeding the cells.
   b. Edge effect at the plate, cause extensive evaporation of the medium at the edge perimeter of the plate. Supply perimeter wells with PBS;
   avoid seeding cells at the edge wells.
2. Inconsistency in ATP level between different plates, which were treated similarly or inconsistency in control wells in different plates. This might arise from different incubation times with the CTG reagent, or different volumes of medium or CTG reagent, especially in large high throughput screens. It is helpful to break a large experiment to a few parts, at the CTG reaction step; so all the plates get the same time of lysis and ATP reaction with the reagent.
3. Similar values of viability between plates with high- and low-attachment surfaces. Commercially available low-attachment plates are usually very efficient at keeping the cells unattached to the well surfaces. Yet, some of the plates that we have examined had a compromised ability to support low-attachment growth and cells managed to adhere to the surfaces. If the plates are clear it is useful to visualize growth in suspension and make sure the cells do not attach.
4. Low luminescence signals—this might happen when the cell number is too low or the reader is not working properly. Using a gradient of ATP in known molarity mixed into growth media would help to define ideal cell concentration range and to confirm a functional reader.
5. All the treatments in a time point have the same ATP reads—this might resulted due to inappropriate treatment to the plates; if the plates were sealed and frozen in each time point, it might be helpful to include a few wells filled with ATP in each plate. If all the ATP wells, from different plates, will be similar in reading—it would indicate that the sealing and freezing were done appropriately. If the reads were very different it would be beneficial to check how the plates were freeze in each time point.

C. Anticipated Results

Figure 17:
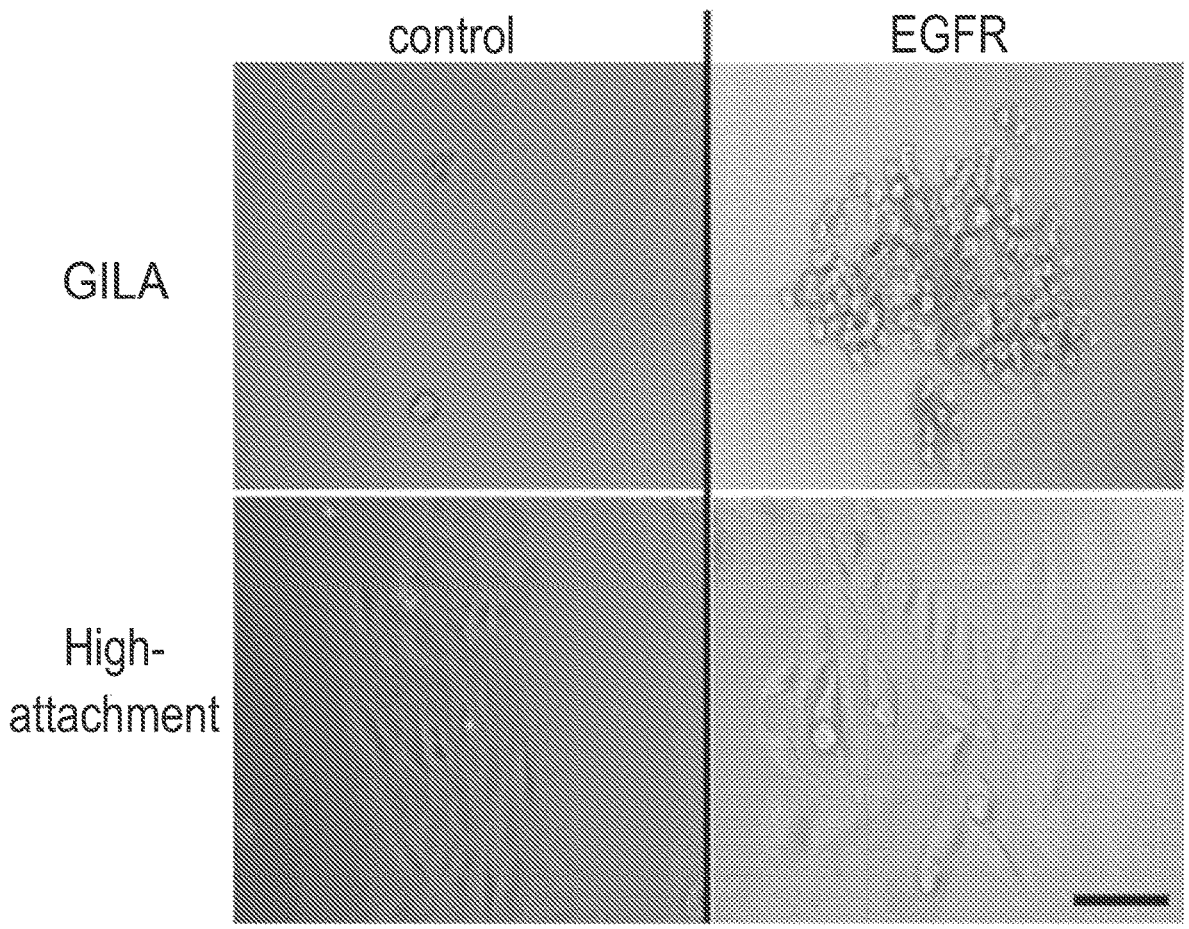
FIG. 17 is a set of images showing the ability to detect cellular aggregates using a GILA assay when an oncogene is introduced to cells.

After optimizing cell concentration and experiment time, it would be helpful to measure growth in low attachment of transformed cell line alongside its non-transformed counterpart line. If the above mentioned parameters were optimized, it would be anticipated to detect a maximal difference in viability (MDV) at one time point between transformed and non-transformed cell lines (FIG. 15). This MDV defines the optimal conditions for future experiments with the tested cell lines, given that the non-transformed cells are in decreasing viability course while transformed cells growing in a logarithmic growth scale. An example for this difference in GILA can be easily detected by the cellular aggregates when an oncogenic ORF is expressed (FIG. 17).

Tumor ex vivo cultures may demonstrate a higher degree of variability in growth and composition of outgrowing cells. Since transformed cells will have a growth advantage over other cells of the tumor microenvironment (such as tumor-infiltrating lymphocytes) it is expected that most cells growing in the GILA platform are indeed tumor cells. This is well suited to test the cell-autonomous responses to genome editing or pharmacological challenges, while to a certain degree one may also be able to investigate cell-to-cell interactions between tumor and cancer-associated fibroblasts or other cells of the tumor microenvironment. One would expect that the more rapidly proliferating tumor cells on the GILA platform demonstrate a higher growth rate compared to the regular attachment plates, and therefore measure a difference in viability or MDV. Future development of the GILA platform may be aimed to optimize growth conditions for both, tumor cells and all of the cells of the microenvironment, in order to best reflect the tumor composition in vivo.

D. Time Considerations

To complete a full protocol for the basic procedure of seeding and growing the cells on low attachment surfaces followed by viability assessment will require about 5 days. From these 5 days the hands-on time will differ according to the step and would be around the indicated time frames: seeding the cells—1 hour, inspect for contaminations—15 minutes, lyse the cells and read luminescence—1 hour. For a pharmacological screen, it would be reasonable to add one additional day on top of the 5 days. This takes into consideration the extra day required for the cells to settle into the wells after seeding and before drug treatment. From that day the cells will be incubated for the standard time range, as set at the basic protocol. With the addition of a genetic perturbation screen to the basic protocol, one can expect to extend the procedure to about 15 days, with the additional time needed to ensure selection of gene-expressing cells and time to process the cells at the end of the assay for their barcodes.

Example 3—Ex Vivo Sample Assay

This embodiment demonstrates the application of the growth in low attachment technology to detect drug sensitivity of tumor cells in a clinical environment.

Fresh tumors were dissociated and treated to exclude red blood cells. Tumor cells were cultured on high- and low-attachment surfaces and drugs were added after 1 day. At day 4 the cells were lysed and cellular ATP was measured as a surrogate of cell viability. Drug sensitivity of cells to a specific drug was compared between cells that grew on high- and low-attachment surfaces.

Several metastatic melanoma patients were sampled and fresh cells were treated with 4 targeted drugs specific for the RAF/MEK pathway; Dabrafenib (BRAF inhibitor), Trametinib (MEK1/2 inhibitor), SCH772984 (ERK1/2 inhibitor) and VX-11e (ERK2 inhibitor).

Patient number 1—GILA assay revealed that this specific individual might benefit from ERK1/2 inhibitors. The GILA assay was 10 times more sensitive at predicting this drug sensitivity than the traditional high-attachment method.

Patient number 2—The cells were tested for sensitivity to the four drugs and were found to be sensitive to all four. Again, the GILA assay was 10 times more sensitive compared to the assay that was performed on high-attachment surfaces. Another laboratory has studied the same sample with the same four drugs and found similar results: this specific tumor was sensitive to all four drugs. The results from the collaborating laboratory were generated in a different experimental system and focused on apoptosis as a result of drug cytotoxicity. These similar sensitivity patterns that were found by two different assays highlight the efficiency of the GILA assay.

Patient number 3—Melanoma cells from this patient were sensitive to MEK-inhibitor and ERK1/2 inhibitors but not completely to BRAF inhibitors. The GILA assay was more sensitive when ERK1/2 inhibitors were used.

The GILA method is a 3-dimensional assay (3D) that was shown to be more sensitive as compared to the traditional growth on high-attachment surfaces (2D). This advantageous technology is specifically aimed at tumor cells and was tested using both cancer cell lines and patient-derived cells.

Microfluidics device—In order to perform the GILA assay in very small volumes, and when the sample is very limited (like with biopsy or fine needle aspirate), we replicated the technology in microfluidic devices. We optimized the necessary conditions to maintain cells for a few weeks in a microfluidic device, flow toxic reagent into the device and were able to document the effect on the cells.

Device measurements—star shape, double layer PDMS, 2 chambers on each side of the star with 1 inlet and 1 outlet for each.

All publications, patents, and patent applications mentioned herein are incorporated by reference to the same extent as if each individual publication, patent or patent application was specifically and individually indicated to be incorporated by reference in its entirety. In the event of there being a difference between definitions set forth in this application and those in documents incorporated herein by reference, the definitions set forth herein control. Various modifications and variations of the described methods, pharmaceutical compositions, and kits of the disclosure will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

We claim:

1. A method for identifying an agent that inhibits cellular growth and/or viability of tumorigenic or transformed cells in combination with a genetic perturbation, the method comprising:
providing a cellular sample of transformed cells and/or cells obtained from the tumor of a subject, wherein the transformed cells and/or cells obtained from the tumor are adherent cells;
infecting the cells with a barcoded library of lentiviruses encoding one or more CRISPR genetic perturbations, wherein the barcode identifies the one or more CRISPR genetic perturbations;
culturing the cellular sample for at least 5 days under low attachment conditions comprising agitating the cells, wherein the conditions inhibit cell attachment to the culture surface;
contacting or incubating the cellular sample with the agent; and
identifying the one or more genetic perturbations that are depleted in the sample contacted with the agent as compared to a control not contacted with the agent, whereby the agent inhibits cellular growth and/or viability of tumorigenic or transformed cells in combination with the one or more depleted genetic perturbations.

2. The method of claim 1, wherein the tumor is a solid tumor.

3. The method of claim 1, wherein the agent is a chemical compound, a small molecule, or an antibody.

4. The method of claim 1, wherein the cells are aliquoted into one or more containers,
wherein the containers are the wells of a microtiter plate, or
wherein the containers comprise one or more mixing circuits of a microfluidic device.

5. The method of claim 4, wherein the mixing circuit comprises a pneumatically actuated pump for circulating cells in the mixing circuit; and/or
wherein the mixing circuit comprises one or more valves configured to act in concert to circulate the cells around the mixing circuit,
thereby inhibiting attachment of the cells to internal surfaces of the microfluidic device.

6. The method of claim 4, wherein the individual wells of the microtiter plate or individual mixing circuits of the microfluidic device are treated with different test agents, and/or concentrations of test agents.

7. The method of claim 4, wherein the microfluidic device comprises an input port in fluid connection with the mixing circuit;
a holding chamber in fluid communication with the mixing circuit;
an output port; and/or
one or more additional valves.

8. The method of claim 7, wherein at least one of the one or more valves is a sieve valve; and/or
wherein at least one or more of the valves is a conventional valve; and/or
wherein a valve is positioned between the input port and the mixing circuit; and/or
wherein one or more valves is positioned between the mixing circuit and the holding chamber; and/or
wherein one or more valves is positioned between the mixing circuit, the holding chamber and the output port; and/or
wherein one or more valves are positioned between the two or more mixing circuits.

9. The method of claim 4, further comprising splitting the cellular sample between two or more microfluidic mixing circuits of the microfluidic device, wherein a different test agent is loaded into each microfluidic mixing circuit, before, after, or concurrent with the cellular sample.

10. The method of claim 1, wherein culturing under low attachment conditions comprises culturing the cells on a surface treated with at least one compound that inhibits cell attachment.

11. The method of claim 1, wherein culturing under low attachment conditions comprises culturing the cells on an ultra-low attachment surface.

12. The method of claim 1, wherein the genetic perturbation is a gene knock-in, a gene knock-out, one or more nucleotide insertions, deletions, substitutions, or mutations, or a combination thereof.

* * * * *

UNITED STATES PATENT AND TRADEMARK OFFICE
CERTIFICATE OF CORRECTION

Page 1 of 2

PATENT NO. : 11,807,895 B2
APPLICATION NO. : 15/560977
DATED : November 7, 2023
INVENTOR(S) : Asaf Rotem et al.

It is certified that error appears in the above-identified patent and that said Letters Patent is hereby corrected as shown below:

On the Title Page

In item (73), in Column 1, in "Assignee", Lines 2-3, delete "DANA FARBER" and insert
-- DANA-FARBER --.

In item (57), in Column 2, in "Abstract", Line 7, delete "and7or" and insert -- and/or --.

In item (57), in Column 2, in "Abstract", Line 11, delete "a n" and insert -- an --.

In the Specification

In Column 4, Line 44, delete "FIG. 16." and insert -- FIG. 16 --.

In Column 6, Line 7, delete "non-melonoma)." and insert -- non-melanoma). --.

In Column 7, Line 18, delete "2d" and insert -- 2nd --.

In Column 7, Line 20, delete "3d" and insert -- 3rd --.

In Column 10, Line 42, delete "5-brom-2'-deoxyuridine," and insert -- 5-bromo-2'-deoxyuridine, --.

In Column 20, Lines 10-30, delete "To test whether drugs identified and validated in the drug screen had anti-neoplastic activity in the context of human disease, we isolated fresh, ascites-derived ovarian cancer cells from 5 patients who had failed multiple lines of treatment (FIG. 10). Immediately after procurement, ascites samples were processed and 5000 cells per well were flow-sorted into 96-well microtiter plates with low or high-attachment surfaces containing 100 µl of growth medium per well. These ex-vivo cultures were treated individually with four FDA-approved drugs identified and validated in the drug screen (azelastine hydrochloride and nitazoxanide, RepSox or nobiletin) for 72 hours. Two compounds, azelastine and nitazoxanide, demonstrated inhibitory activity in the GILA assay (FIG. 4A), with a dose dependent response shown for azelastine hydrochloride (FIG. 4B).

Signed and Sealed this
Second Day of April, 2024

Katherine Kelly Vidal
*Director of the United States Patent and Trademark Office*

Interestingly, cancer cells from the various patients displayed differential sensitivity to these drugs. These results validate ex-vivo GILA-based drug screens as a potential tool for drug discovery and repurposing to individually treat cancer patients who have failed to respond to conventional treatment." and insert the same on Column 20, Line 11, as a new paragraph.

In Column 24, Line 62, delete "pit" and insert -- µl --.

In Column 24, Line 63, delete "pit" and insert -- µl --.

In Column 24, Line 64, delete "pit" and insert -- µl --.